US008404233B2

(12) United States Patent
Sunamura et al.

(10) Patent No.: US 8,404,233 B2
(45) Date of Patent: Mar. 26, 2013

(54) NEUTRALIZING MONOCLONAL ANTIBODY AGAINST HUMAN DLL4

(75) Inventors: Makoto Sunamura, Tokyo (JP); Hideo Yagita, Tokyo (JP)

(73) Assignee: Smart Targeting Limited, London (GB)

( * ) Notice: Subject to any disclaimer, the term of this patent is extended or adjusted under 35 U.S.C. 154(b) by 391 days.

(21) Appl. No.: 12/599,804

(22) PCT Filed: May 15, 2008

(86) PCT No.: PCT/GB2008/001678
§ 371 (c)(1),
(2), (4) Date: Jul. 21, 2010

(87) PCT Pub. No.: WO2008/139202
PCT Pub. Date: Nov. 20, 2008

(65) Prior Publication Data
US 2010/0303812 A1 Dec. 2, 2010

(30) Foreign Application Priority Data
May 15, 2007 (GB) .................................. 0709333.9

(51) Int. Cl.
| | | |
|---|---|---|
| A61K 39/395 | (2006.01) | |
| C07K 16/18 | (2006.01) | |
| C07H 21/04 | (2006.01) | |
| C12P 21/00 | (2006.01) | |
| C12P 21/08 | (2006.01) | |
| C12N 5/00 | (2006.01) | |
| C12N 15/00 | (2006.01) | |
| C12N 15/09 | (2006.01) | |
| C12N 15/13 | (2006.01) | |

(52) U.S. Cl. ............... 424/130.1; 424/133.1; 424/134.1; 424/138.1; 424/141.1; 424/145.1; 424/152.1; 424/158.1; 424/178.1; 435/69.1; 435/70.1; 435/235.1; 435/320.1; 435/325; 435/328; 435/330; 435/335; 435/336; 530/387.1; 530/387.3; 530/387.7; 530/388.1; 530/388.24; 514/13.3; 514/19.2; 536/23.53

(58) Field of Classification Search .................. None
See application file for complete search history.

(56) References Cited

U.S. PATENT DOCUMENTS

| | | | | |
|---|---|---|---|---|
| 5,985,281 | A * | 11/1999 | Taylorson et al. | 424/178.1 |
| 8,192,738 | B2 * | 6/2012 | Bedian et al. | 424/130.1 |
| 2006/0134121 | A1 | 6/2006 | Thurston et al. | |
| 2008/0014196 | A1 * | 1/2008 | Yan | 424/133.1 |
| 2010/0119526 | A1 * | 5/2010 | Hellstrom | 424/172.1 |

FOREIGN PATENT DOCUMENTS

| | | |
|---|---|---|
| WO | WO-2005012359 A2 | 2/2005 |
| WO | WO-2007028110 A2 | 3/2007 |
| WO | WO-2007048849 A1 | 5/2007 |
| WO | WO-2007070671 A2 | 6/2007 |
| WO | WO-2007143689 A2 | 12/2007 |
| WO | WO-2008019144 A2 * | 2/2008 |

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Kaufman et al. Blood 94: 3178-3184, 1999.*
Wang et al. Rapid analysis of gene expression (RAGE) facilitates universal expression profiling. Nucleic Acids Res 27(23): 4609-4618, 1999.*
Wigley et al. Site-specific transgene insertion: an approach. Reprod Fertil Dev 6: 585-588, 1994.*
Phillips, A., The challenge of gene therapy and DNA delivery. J Pharm Pharmacology 53: 1169-1174, 2001.*
Oishi et al. Blockade of delta-like ligand 4 signaling inhibits both growth and angiogenesis of pancreatic cancer. Pancreas 39: 897-903, 2010.*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Colman (Research in Immunol. 145:33-36 (1994)).*
Rubanyi, G.M. The future of human gene therapy. Mol Aspects Med 22: 113-142, 2001.*
Juengst, E.T. What next for human gene therapy? BMJ 326: 1410-1411, 2003.*
Fukuda et al. Notch ligand Delta-like 4 blockade attenuates atherosclerosis and metabolic disorders. Proc Natl Acad Sci USA; published online Jun. 13, 2012; pp. E1868-E1877.*
International Search Report and Written Opinion of the International Searching Authority for PCT/GB2008/001678 mailed Sep. 3, 2008 (15 pp.).
Ridgway, John et al: "Inhibition of DLL4 signalling inhibits tumour growth by deregulating angiogenesis", Nature Publishing Group, Dec. 1, 2006, vol. 444, No. 7122, pp. 1083-1087.

(Continued)

Primary Examiner — Bridget E Bunner
(74) Attorney, Agent, or Firm — Harris Beach PLLC

(57) ABSTRACT

The present invention provides a binding protein capable of binding to delta-like ligand 4 (DLL4) as well as methods and uses thereof in therapy, diagnosis or imaging. Also provided are fusion proteins and protein conjugates, nucleic acid molecules encoding the binding proteins and methods of preparing binding proteins capable of binding to DLL4.

18 Claims, 10 Drawing Sheets

OTHER PUBLICATIONS

Noguera-Troise, Irene et al: "Blockade of DLL4 inhibits tumour growth by promoting non-productive angiogenesis", Nature Publishing Group, vol. 444, No. 7122, Dec. 1, 2006, pp. 1032-1037.

Xu F., et al: "Intraovarian actions of anti-angiogenic agents disrupt periovulatory events during the menstrual cycle in monkeys", Contraception, vol. 71, No. 4., Apr. 1, 2005, pp. 239-248.

Holt, L.J. et al: "Domain antibodies: proteins for therapy", Trends in Biotechnology, vol. 21, No. 11, Nov. 2003, pp. 484-490.

Davies, J., et al: "Affinity improvement of single antibody VH domains: residues in all three hypervariable regions affect antigent binding", Immunotechnology, vol. 2, No. 3, Sep. 1, 1996, pp. 169-179.

Sainson, Richard C.A., et al: "Anti- DLL4 therapy: can we block tumour growth by increasing angiogenesis?", Trends in Molecular Medicine, vol. 13, No. 9, Jan. 1, 2007, pp. 389-395.

Thurston, G., et al: "The Delta Paradox: DLL4 blockade leads to more tumour vessels but less tumour growth", Nature Reviews. Cancer, vol. 7, No. 5, May 1, 2007, pp. 327-331.

Lobov, I.B., et al: "Delta-like ligand 4 (Dll4) is induced by VEGF as a negative regulator of angiogenic sprouting", Proceeds of the National Academy of Sciences of USA, vol. 104, No. 9, Feb. 27, 2007, pp. 3219-3224.

Liu, Zhao-Jun et al: "Regulation of Notch1 and DLL4 by Vascular Endothelial Growth Factor in Arterial Endothelial Cells: Implications for Modulating Arteriogenesis and Angiogenesis", Molecular and Cellular Biology, Jan. 1, 2003, vol. 23 No. 1, pp. 14-25.

* cited by examiner

A

B

NEUTRALIZING MONOCLONAL ANTIBODY AGAINST HUMAN DLL4

This application is a national stage application under 35 U.S.C. §371 of PCT Application No. PCT/GB2008/001678 filed May 15, 2008, which claims priority to and the benefit of United Kingdom patent application Serial No. 0709333.9, filed May 15, 2007, which is incorporated herein by reference in its entirety.

FIELD OF THE INVENTION

The invention relates to anti-angiogenic binding proteins and all uses thereof. In particular, the invention relates to antibodies or antibody fragments specific for delta-like ligand 4 (DLL4) and to uses thereof.

BACKGROUND

Angiogenesis, i.e. the formation of new blood vessels from pre-existing ones, is a complex process which has a fundamental role during embryogenesis, wound healing, and reproductive functions. In a healthy subject, angiogenesis is highly regulated, being turned on for brief periods when required, and then completely inhibited. Failures in the regulation of angiogenesis can have deleterious consequences and many diseases such as atherosclerosis, arthritis, ocular neovascularisation and cancer are typically characterised by persistent angiogenesis.

In the case of solid tumours, the development of an adequate vasculature to deliver nutrients and oxygen to tumour cells is very important. Solid tumour cells depend on angiogenesis for their growth much more than normal cells and tumours can grow progressively only if they can vascularise themselves. Therefore, control of vascular development could permit new therapeutic approaches to cancer.

The Notch pathway is an evolutionarily conserved intercellular signalling pathway which is involved in various biological processes including cell fate determination, cellular differentiation, proliferation, survival and apoptosis. The Notch receptor is believed to play an important part in angiogenesis. There are four different mammalian Notch receptors and several different Notch ligands, including delta-like-1, delta-like 4 (DLL4), Jagged1 and Jagged2.

DLL4 is a transmembrane protein of about 685-amino acids, comprising an extracellular region which contains 8 EGF-like repeats and a DSL domain characteristic of Notch ligands. DLL4 also has a transmembrane domain and a cytoplasmic tail apparently lacking any catalytic motifs. Human DLL4 shares 87% amino acid sequence identity with mouse DLL4. DLL4 is also referred to in the art as "Dll4" and throughout this text "DLL4" and "Dll4" are used interchangeably.

The gene which encodes murine DLL4 has been sequenced and the sequence has been deposited under accession number NM_019454. This sequence is designated herein as SEQ ID NO: 19. The sequence of the corresponding protein can be found under the same accession number and it is designated herein as SEQ ID NO: 20.

The gene which encodes human DLL4 has been sequenced and the sequence has been deposited under accession number NM_019074. This sequence is designated herein as SEQ ID NO: 21. The sequence of the corresponding protein can be found under the same accession number and it is designated herein as SEQ ID NO: 22.

DLL4 can interact inter alia with receptors designated Notch1, Notch2, Notch3 and Notch4. In mice, haploinsufficiency of delta-like 4 ligand results in embryonic lethality due to major defects in arterial and vascular development. DLL4 is therefore likely to play an important part in angiogenesis.

DLL4 activity is primarily regulated at the gene expression level. The main regulator is vascular endothelial growth factor (VEGF) via the phosphatidylinositol 3-kinase/Akt pathway.

The biological function of DLL4 in primary endothelial cells and the expression of DLL4 in renal cancer was investigated by Patel et al. (Cancer Research 2005; 65:19, pages 8690-8697). These workers suggest that selective modulation of DLL4 expression within human tumours may represent a potential anti-angiogenic therapy.

Probably the best-studied and most advanced approach to anti-angiogenic therapy is VEGF inhibition. The humanized monoclonal antibody (mAb) bevacizumab (Avastin) is to our knowledge the only anti-angiogenic antibody approved for the treatment of cancer (Presta L. G. "Humanization of an anti-vascular endothelial growth factor monoclonal antibody for the therapy of solid tumour and other disorder". Cancer Res., 57: 4593-4599, 1997 and Ferrara N. "VEGF as a therapeutic target in cancer." Oncology, 69: 11-16, 2005). Bevacizumab was developed from a murine mAb to human VEGF and was selected for clinical development based on preclinical evidence showing high anti-angiogenic and anti-tumour activity (Borgstrom P. "Complete inhibition of angiogenesis and growth of microtumours by anti-vascular endothelial growth factor neutralizing antibody: Novel concepts of angiostatic therapy from intravital videomicroscopy." Cancer Res., 56: 4032-4039, 1996).

There remains a need for further agents which can modulate angiogenesis, in particular in the context of cancer therapy.

DETAILED DESCRIPTION OF THE INVENTION

The present inventors have generated three neutralising monoclonal antibodies (mAbs) against human DLL4 by immunising a BALB/c mouse with recombinant soluble human DLL4 (Serine 27 to Proline 524 of the extracellular domain of native human DLL4, obtained from R&D Systems, Inc. 614 McKinley Place Nebr., Minneapolis, Minn. 55413, USA) as described in the Examples section.

The inventors have cloned and sequenced the antibodies and determined the sequence of the antibody light and heavy chain variable regions ($V_H$ and $V_L$) and complementarity determining regions (CDR) 1, 2 and 3.

Amino acid and/or DNA sequences of antibody molecules which can specifically bind to human DLL4 and their $V_H$ and $V_L$ domains and CDRs, or nucleotide sequences encoding them, are set forth in the various SEQ ID Nos. listed herein.

In one aspect, the present invention provides a binding protein capable of binding to human DLL4, which binding protein comprises a light chain CDR 1 comprising or consisting of the amino acid sequence RASSSVSFMH (SEQ ID NO; 6), or a sequence substantially homologous thereto; and/or comprises a light chain CDR 2 comprising or consisting of the amino acid sequence ATSNLTS (SEQ ID NO: 7), or a sequence substantially homologous thereto; and/or comprises a light chain CDR3 comprising or consisting of the amino acid sequence QQWSSNPFT (SEQ ID NO: 8), or a sequence substantially homologous thereto; and/or comprises a heavy chain CDR1 comprising or consisting of the amino acid sequence SYVMH (SEQ ID NO. 3), or a sequence substantially homologous thereto; and/or comprises a heavy chain CDR2 comprising or consisting of the amino acid sequence YIIPYNDGTKYNEKFKG (SEQ ID NO. 4), or a sequence substantially homologous thereto; and/or comprises a heavy chain CDR3 comprising or consisting of the amino acid sequence SEDYDHFDY (SEQ ID NO: 5), or a sequence substantially homologous thereto.

The term "light chain CDR" and "heavy chain CDR" is used herein for the purpose of nomenclature and does not imply that the binding protein has a definable light and/or heavy chain, or even that the particular CDR is found on a heavy or light chain if such identifiable parts are present.

Preferred binding proteins comprise two or more of the light chain CDRs of the invention or sequences substantially homologous thereto as described above. Especially preferred binding molecules comprise 3 of the light chain CDRs of the invention or sequences substantially homologous thereto as described above (i.e. one of each of the light chain CDR1 and CDR2 and CDR3).

Other preferred binding proteins comprise two or more of the heavy chain CDRs of the invention or sequences substantially homologous thereto as described above. Especially preferred binding molecules comprise 3 of the heavy chain CDRs of the invention or sequences substantially homologous thereto as described above (i.e. one of each of the heavy chain CDR1 and CDR2 and CDR3).

Preferably, the binding protein comprises at least one heavy chain CDR and at least one light chain CDR of the invention or sequences substantially homologous thereto. More preferably, the binding protein comprises at least two heavy chain CDRs and at least two light chain CDRs of the invention or sequences substantially homologous thereto.

Especially preferred binding molecules comprise a heavy chain CDR1 domain of SEQ ID NO: 3, a CDR2 domain of SEQ ID NO: 4, and a CDR3 domain of SEQ ID NO: 5, or sequences substantially homologous thereto; and comprise a light chain CDR1 domain of SEQ ID NO: 6, a CDR2 domain of SEQ ID NO: 7, and a CDR 3 domain of SEQ ID NO: 8, or sequences substantially homologous thereto.

Further preferred embodiments provide binding proteins capable of binding to human DLL4, comprising a $V_H$ (variable heavy chain) domain which comprises one or more of the heavy chain CDRs of the invention or sequences substantially homologous thereto, as described above, and/or a $V_L$ (variable light chain) domain which comprises one or more of the light chain CDRs of the invention or sequences substantially homologous thereto, as described above.

Preferred light chain variable regions ($V_L$ domains) comprise 2 or more of the light chain CDRs of the invention or sequences substantially homologous thereto, as described above. Especially preferred $V_L$ domains comprise 3 of the light chain CDRs of the invention or sequences substantially homologous thereto as described above (i.e. one of each of CDR1, CDR2 and CDR3). Preferred heavy chain variable regions ($V_H$ domains) comprise 2 or more of the heavy chain CDRs of the invention or sequences substantially homologous thereto, as described above. Especially preferred $V_H$ domains comprise 3 of the heavy chain CDRs of the invention or sequences substantially homologous thereto as described above (i.e. one of each of CDR1, CDR2 and CDR3). Most preferred binding proteins comprise 3 of the light chain CDRs of the invention or sequences substantially homologous thereto as described above and 3 of the heavy chain CDRs of the invention or sequences substantially homologous thereto as described above.

Any combination of the above discussed $V_L$ and $V_H$ domains can be present in the binding proteins of the invention. Thus, a preferred binding protein of the invention comprises a $V_L$ domain which comprises CDR 1 (SEQ ID NO: 6) and/or CDR 2 (SEQ ID NO: 7) and/or CDR 3 (SEQ ID NO: 8), or sequences substantially homologous thereto, and a $V_H$ domain which comprises CDR 1 (SEQ ID NO: 3) and/or CDR 2 (SEQ ID NO: 4) and/or CDR 3 (SEQ ID NO: 5), or sequences substantially homologous thereto.

A yet further embodiment of the invention provides a binding protein comprising a $V_H$ domain which has the amino acid sequence of SEQ ID NO: 1, or a sequence substantially homologous thereto, and/or a $V_L$ domain which has the amino acid sequence of SEQ ID NO: 2, or a sequence substantially homologous thereto.

An antibody having a $V_H$ domain which has the amino acid sequence of SEQ ID NO: 1 and a $V_L$ domain which has the amino acid sequence of SEQ ID NO: 2 is denoted herein as "STL4".

The term "binding protein" as used herein refers to proteins that specifically bind to another substance. In a preferred embodiment binding proteins are chimeric or humanised proteins. Preferred chimeric proteins are chimeric antibodies and they preferably comprise a human heavy constant domain and a human light constant domain. Preferably, the binding proteins are antibodies or antibody fragments, or comprise antibodies or antibody fragments. Humanised antibodies or antibody fragments are particularly preferred.

The inventors have prepared a chimeric antibody which comprises a heavy chain CDR1 domain of SEQ ID NO: 3, a CDR2 domain of SEQ ID NO: 4, and a CDR3 domain of SEQ ID NO: 5 and a light chain CDR1 domain of SEQ ID NO: 6, a CDR2 domain of SEQ ID NO: 7, and a CDR 3 domain of SEQ ID NO: 8, as well as the human heavy chain constant domain CH1-H—CH2-CH2 and the human light chain constant domain κ (kappa). Details regarding this antibody, termed herein cSTL4, can be found in Example 8.

In another preferred embodiment, the binding protein is an affibody. Affibodies are well known in the art and they are typically small proteins of e.g. about 6 kDa which are composed of a three-helix bundle, originally derived from staphylococcal protein A.

The binding proteins of the present invention are capable of specifically binding to human DLL4 or fragments of human DLL4, or entities comprising human DLL4 or fragments of human DLL4. By "specifically binding" is meant that there is significant binding to DLL4, but less, weaker, or none, preferably significantly less, weaker, or no binding to other (control) antigens. Suitable control antigens may be selected from e.g. DLL1, Jagged1 and Jagged2. Preferably, there is no significant binding to any antigen which is typically present in the human body, other than DLL4. If there is binding to other antigens, this is preferably insignificant and not prohibitive for diagnostic, imaging or therapeutic applications.

By "significant binding" is meant binding which can be measured using standard techniques and which is at least statistically significant. The binding is preferably in a way or at a level that is effective for diagnostic, imaging or therapeutic purposes.

By "insignificant binding" is meant binding which is unmeasurable, or which can be measured using standard techniques but which is statistically and/or physiologically not significant or relevant.

Suitable techniques for testing the binding specificity of a binding protein are known to the skilled person. The skilled person will appreciate that when binding is assayed, suitable concentrations of the binding protein and the target antigen must be used. At very high concentrations there will typically be some or even significant non-specific binding, so the skilled person is aware of suitable concentrations that should be used to assay binding specificity. An example of a suitable technique includes flow cytometry. For example, binding to CHO cells transfected with DLL4 may be compared to binding to non-transfected CHO cells and/or CHO cells transfected with a different antigen, e.g. DLL1, Jagged1 or Jagged2. Other suitable techniques include ELISA, Western Blots and radioimmune assays.

Preferably, the binding proteins have a binding affinity for DLL4 which corresponds to a Kd of less than 5, 4, 3, 2 or 1 µM, more preferably of less than 500, 400 or 300 nM, even more preferably of less than 200, 190, 180, 170, 160, 150, 140, 130, 120, 110, or 100 nM, most preferably of less than 90, 80, 70, 60, 50, 40, 30, 20, 10, 5 or 1 nM. Most preferably, the Kd is less than $10 \times 10^{-10}$ M, even more preferably less than $5 \times 10^{-10}$ M, e.g. about $4 \times 10^{-10}$ M Any appropriate method of determining Kd may be used. However, preferably the Kd is determined by testing various concentrations of the binding protein against a fixed amount of DLL4 (or DLL4-transfected cells) in vitro to establish a saturation curve, for example using the Lineweaver-Burk method or preferably by using commercially available binding model software, such as the BIAcore™ software. A suitable assay is described in Example 9. By "Kd" is meant the calculated dissociation constant, which is also referred to as "$K_D$" in the art.

The binding proteins preferably have a Kd for DLL4 which is at least 0.5 or 1, more preferably at least 2, 3, 4 or 5 orders of magnitude lower than the Kd for another antigen, e.g. (human) DLL1, (human) Jagged1 or (human) Jagged2, when binding affinity is assayed under comparable conditions, in particular using the same dosage of binding protein and antigen (or cells transfected with DLL4 or the control antigen) in each assay.

Preferably, the binding proteins can inhibit or significantly reduce the function of DLL4 or prevent DLL4 interacting with one or more of its natural ligands/receptors, in particular Notch. The binding proteins can thus preferably act as antagonists of DLL4. Binding to ligands or receptors, e.g. Notch, can be assayed using standard techniques known to the skilled person. The binding of free DLL4 to a specific ligand or receptor can be compared to the binding of DLL4 which has been contacted with a binding protein of the present invention. Suitable assay methods include flow cytometry and ELISA. For example, flow cytometry may be used to compare the binding of DLL4 to Notch-transfected CHO cells to the binding of DLL4 which has been contacted with a binding protein of the present invention to Notch-transfected CHO cells.

An alternative suitable method for assaying the effect of an anti-DLL4 antibody on Notch-signalling is described in Example 6. Briefly, a reporter system which is activated by Notch-mediated signalling such as the Notch/CSL reporter may be used and the effect of an anti-Dll4-antibody on the output of the reporter system can be assayed. In the case of the Notch/CSL reporter system, a decrease in luciferase activity is a measure of a decrease in Notch-mediated signalling, indicating that the antibody has an inhibitory effect on Notch-mediated signalling.

Unless specifically stated otherwise, any reference herein to "DLL4" is intended to mean the human form of DLL4.

Any reference herein to "Notch" includes Notch1, Notch2, Notch3 and/or Notch4. Preferably, "Notch" is Notch1.

The term "chimeric" as used herein in connection with antibody molecules and binding proteins refers to binding proteins having constant antibody regions derived from or corresponding to sequences found in one species and variable antibody regions (e.g. $V_H$, $V_L$, CDR or FR regions) derived from another species.

Preferably, the constant antibody regions are derived from or corresponding to sequences found in humans, e.g. in the human germ line or somatic cells and the variable antibody regions (e.g. $V_H$, $V_L$, CDR or FR regions) are derived from sequences found in a non-human animal, e.g. a mouse, rat, rabbit or hamster.

The term "humanised" as used herein in connection with antibody molecules and binding proteins refers to binding proteins having one or more variable (e.g. $V_H$, $V_L$, CDR or FR regions) and/or constant antibody regions derived from or corresponding to sequences found in humans, e.g. in the human germ line or somatic cells. As used herein, the term "humanised" binding protein includes any binding protein which has been modified to reduce its immunogenicity in humans.

Various techniques for humanising antibodies are known in the art. An example includes the resurfacing method described by Roguska et al. "Humanization of murine monoclonal antibodies through variable domain resurfacing." Proc Natl Acad Sci USA. 1994 Feb. 1; 91(3):969-73. Resurfacing may be used to change the patterns of surface accessible residues in the Fv (variable fragment) regions of the murine antibodies to resemble those found on the Fv regions of human antibody sequences. Another technique involves CDR-grafting, where the CDR regions of the murine antibody are combined with human framework regions (FRs). The human FRs may be selected e.g. by selection from human consensus sequences, or by selection from individual human antibodies.

The "humanised" binding proteins of the invention may include amino acid residues not encoded by human sequences, e.g. mutations introduced by random or site directed mutations in vitro (in particular mutations which involve conservative substitutions or mutations in a small number of residues of the binding protein, e.g. in 1, 2, 3, 4 or 5 of the residues making up one or more of the CDRs of the binding protein). In addition, the human binding proteins of the present invention include proteins comprising human consensus sequences identified from human sequences.

The humanised binding proteins of the present invention are not limited to combinations of $V_H$, $V_L$, CDR or FR regions which are themselves found in combination in human antibody molecules. Thus, the humanised binding proteins of the invention may include or correspond to combinations of such regions which do not necessarily exist naturally in humans.

The term "antibody" or "antibody molecule" as used herein refers to immunoglobulin molecules.

The term "antibody" or "antibody molecule" as used herein is thus intended to include whole antibodies (e.g. IgG, IgA, IgE, IgM, or IgD), monoclonal antibodies, polyclonal antibodies, humanised and chimeric antibodies and antibodies with modified Fc regions. Antibody fragments which comprise an antigen binding domain are also included.

The term "antibody fragment" as used herein is intended to include any appropriate antibody fragment that displays antigen binding function, for example Fab, Fab', F(ab')$_2$, scFv, Fv, dsFv, ds-scFv, Fd, dAbs, camelised antibodies, TandAbs dimers, minibodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art.

The antibodies or antibody fragments can be produced naturally or can be wholly or partially synthetically produced. Thus the antibody may be from any appropriate source, for example recombinant sources and/or produced in transgenic animals or transgenic plants. Thus, the antibody molecules can be produced in vitro or in vivo.

Preferably the antibody or antibody fragment comprises an antibody light chain variable region ($V_L$) and an antibody heavy chain variable region ($V_H$) which generally comprise the antigen binding site. In certain embodiments, the antibody or antibody fragment comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region. The Fc region may be modified in some way to influence its function, for example to modify its interaction with immune effector functions such as Fc receptors or the C1 component of complement. Furthermore, the antibody or antibody fragment can comprise all or a portion of a kappa light chain constant region or a lambda light chain constant region. Preferably, the light chain constant region is a kappa light chain constant region. All or part of such constant regions may be produced naturally or may be wholly or partially synthetic. Appropriate sequences for such constant regions are well known and documented in the art.

The term "fragment" as used herein refers to fragments of biological relevance; e.g. fragments which can contribute to antigen binding, e.g. form part of the antigen binding site, or can contribute to the inhibition or reduction in function of the antigen, or can contribute to the prevention of the antigen interacting with its natural receptor. Preferred fragments thus comprise a heavy chain variable region ($V_H$ domain) and/or a light chain variable region ($V_L$ domain) of the antibodies of the invention. Other preferred fragments comprise one or more of the heavy chain complementarity determining regions (CDRs) disclosed herein, and/or one or more of the light chain complementarity determining regions (CDRs) disclosed herein.

In embodiments where the binding proteins of the invention comprise a fragment of any of the defined sequences (for example comprise a fragment of SEQ ID Nos: 1 or 2), e.g. are binding proteins comprising $V_H$ and/or $V_L$ domains of the invention, or are binding proteins comprising one or more CDRs of the invention, then these regions/domains are generally separated within the binding protein so that each region/domain can perform its biological function and so that the contribution to antigen binding is retained. Thus, the $V_H$ and $V_L$ domains may be separated by appropriate scaffold sequences/linker sequences and the CDRs may be separated by appropriate framework regions such as those found in naturally occurring antibodies. Thus, the $V_H$, $V_L$ and individual CDR sequences of the invention can be provided within, or incorporated into, an appropriate framework or scaffold to enable antigen binding. Such framework sequences or regions can correspond to naturally occurring framework regions, FR1, FR2, FR3 and/or FR4, as appropriate to form an appropriate scaffold, or can correspond to consensus framework regions, for example identified by comparing various naturally occurring framework regions. Alternatively, non-antibody scaffolds or frameworks, e.g. T cell receptor frameworks can be used. Scaffolds may be used from proteins which do not normally bind antigen, e.g. cytotoxic T-lymphocyte-associated protein 4 (CTLA4).

Appropriate sequences which can be used for framework regions are well known and documented in the art and any of these may be used. Preferred sequences for framework regions are one or more of the framework regions making up the $V_H$ and/or $V_L$ domains of the invention, i.e. one or more of the framework regions disclosed in SEQ ID Nos 9, 10, 11, 12, 13, 14, 15 or 16, or framework regions substantially homologous thereto, and in particular framework regions which allow the maintenance of antigen specificity, for example framework regions which result in substantially the same 3D structure of the binding protein. In preferred embodiments, all four FR regions of SEQ ID NOs: 9, 10, 11 and 12, or FR regions substantially homologous thereto, and/or all four FR regions of SEQ ID NOs: 13, 14, 15 and 16 are found in the binding proteins of the invention.

In addition, although preferred binding proteins of the invention are made up of $V_H$, $V_L$ or CDRs of the invention, it should be noted that the binding proteins of the invention also encompass one or more $V_H$, $V_L$ or CDRs of the invention in combination with other $V_H$, $V_L$ or CDRs not of the invention, provided that the ability to bind to DLL4 is still present. Preferably, the binding specificity for the antigen DLL4 is also still present. Most preferably, the ability to prevent DLL4 from interacting with Notch is also present.

The term "heavy chain complementarity determining region" as used herein refers to regions of hypervariability within the heavy chain variable region ($V_H$ domain) of an antibody molecule. The heavy chain variable region has three complementarity determining regions termed heavy chain complementarity determining region 1, heavy chain complementarity determining region 2 and heavy chain complementarity determining region 3 from the amino terminus to carboxy terminus. The heavy chain variable region also has four framework regions (FR1, FR2, FR3 and FR4 from the amino terminus to carboxy terminus). These regions separate the CDRs.

The term "heavy chain variable region" ($V_H$ domain) as used herein refers to the variable region of a heavy chain of an antibody molecule.

The term "light chain complementarity determining region" as used herein refers to regions of hypervariability within the light chain variable region ($V_L$ domain) of an antibody molecule. Light chain variable regions have three complementarity determining regions termed light chain complementarity determining region 1, light chain complementarity determining region 2 and light chain complementarity determining region 3 from the amino terminus to the carboxy terminus. The light chain variable region also has four framework regions (FR1, FR2, FR3 and FR4 from the amino terminus to carboxy terminus). These regions separate the CDRs.

The term "light chain variable region" ($V_L$ domain) as used herein refers to the variable region of a light chain of an antibody molecule.

Nucleic acid molecules comprising sequences encoding the binding proteins of the invention as defined above, or nucleic acid molecules substantially homologous thereto, form a yet further aspect of the invention. Preferred nucleic acid molecules are as defined in SEQ ID NOS: 17 or 18, or nucleic acid molecules substantially homologous thereto.

The nucleic acid molecules of the invention may be used for antibody production and it may be desirable to optimise the sequence better to comply with the preferred codon usage of the expression host. Such optimisation involves replacing infrequently used codons with more frequently used codons and so it involves changes to the nucleic acid sequence which do not affect the amino acid sequence of the encoded polypeptide. Information regarding the preferred codon usage of expression hosts is widely available and standard methods of altering nucleic acid sequence may be used to arrive at an optimised sequence. Sequences based on SEQ ID Nos: 17 or 18 which have been codon-optimised comprise a further preferred embodiment of the present invention.

Fragments of the binding proteins of the invention as defined above, or sequences substantially homologous thereto, form a yet further aspect of the invention.

Accordingly, the invention provides a polypeptide comprising or consisting of a $V_L$ domain of the invention as defined above, or a sequence substantially homologous thereto, or a polypeptide comprising or consisting of a $V_H$ domain of the invention as defined above, or a sequence substantially homologous thereto wherein the polypeptide is capable of binding to DLL4.

The invention further provides a polypeptide comprising or consisting of one or more of the CDR regions of the invention as defined above, or sequences substantially homologous thereto wherein the polypeptide is capable of binding to DLL4.

Nucleic acid molecules comprising sequences encoding such fragments of the binding proteins of the invention, or nucleic acid molecules substantially homologous thereto, form a yet further aspect of the invention. Preferred nucleic acid sequences encoding such fragments (e.g. $V_H$ domains, $V_L$ domains, and individual CDRs) can be found in SEQ ID NOS: 17 or 18.

The term "substantially homologous" as used herein in connection with an amino acid or nucleic acid sequence includes sequences having at least 50%, preferably at least 60%, more preferably at least 70%, most preferably at least 80%, and even more preferably at least 90%, 95%, 96%, 97%, 98% or 99%, sequence identity to the amino acid or nucleic acid sequence disclosed. Substantially homologous sequences of the invention thus include single or multiple base or amino acid alterations (additions, substitutions, insertions or deletions) to the sequences of the invention. At the amino acid level, preferred substantially homologous sequences contain less than 5, 4, 3, 2 or 1, preferably only 1 or 2, altered amino acids, in one or more of the framework regions and/or one or more of the CDRs making up the sequences of the invention. Preferably said alterations are conservative amino acid substitutions.

A sequence substantially homologous to the light chain CDR1 may therefore preferably be selected from
KASSSVSFMH (SEQ ID NO: 23), RASSTVSFMH (SEQ ID NO: 24), RASSSVTFMH (SEQ ID NO: 25), RATSSVSFMH (SEQ ID NO: 26), RASTSVSFMH(SEQ ID NO: 27), RASSSASFMH (SEQ ID NO: 28), RVSSSVSFMH (SEQ ID NO: 29), RVSSSASFMH (SEQ ID NO: 30), KASSSASFMH (SEQ ID NO: 31), RVSSTVSFMH (SEQ ID NO: 32), RASSSASFMH (SEQ ID NO: 33) or RASSSVSWMH(SEQ ID NO: 34); a sequence substantially homologous to the light chain CDR2 may preferably be selected from
VTSNLTS (SEQ ID NO: 35), ATTNLTS (SEQ ID NO: 36), ATSNLTT (SEQ ID NO: 37), ATSQLTS (SEQ ID NO: 38), ATSNITS (SEQ ID NO: 39), ASSNLTS (SEQ ID NO: 40), ATSNLSS (SEQ ID NO: 41) or VTSNITS (SEQ ID NO: 42);
a sequence substantially homologous to the light chain CDR3 may preferably be selected from
NQWSSNPFT (SEQ ID NO: 43), QNWSSNPFT (SEQ ID NO: 44), QQFSSNPFT (SEQ ID NO: 45), QQWTSNPFT (SEQ ID NO: 46), QQWSTNPFT (SEQ ID NO: 47), QQWSSQPFT (SEQ ID NO: 48), QQWSSNPWT (SEQ ID NO: 49), QQWSSNPFS (SEQ ID NO: 50), NQWSTNPFT (SEQ ID NO: 51), NNWSSNPFT (SEQ ID NO: 52) or QQWTTNPFT (SEQ ID NO: 53); a sequence substantially homologous to the heavy chain CDR1 may preferably be selected from TYVMH (SEQ ID NO: 54), STVMH (SEQ ID NO: 55), SYAMH (SEQ ID NO: 56), SYVML (SEQ ID NO: 57) or TYAMH (SEQ ID NO: 58); a sequence substantially homologous to the heavy chain CDR2 may preferably be selected from
YLIPYNDGTKYNEKFKG (SEQ ID NO: 59), YILPYNDGTKYNEKFKG (SEQ ID NO: 60), YIIPYQDGTKYNEKFKG (SEQ ID NO: 61), YIIPYNEGTKYNEKFKG (SEQ ID NO: 62), YIIPYNDGSKYNEKFKG (SEQ. ID NO: 63), YIIPYNDGTRYNEKFKG (SEQ ID NO: 64), YIIPYNDGTKYQEKFKG (SEQ ID NO: 65), YIIPYNDGTKYNDKFKG (SEQ ID NO: 66), YIIPYNDGTKYNEKWKG (SEQ ID NO: 67), YIIPYNDGTKYNEKFRG (SEQ ID NO: 68), YLLPYNDGTKYNEKFKG (SEQ ID NO: 69), YILPYNDGTKYNEKFKG (SEQ ID NO: 70) or YILPYNEGTKYQEKFKG (SEQ ID NO: 71);

a sequence substantially homologous to the heavy chain CDR3 may preferably be selected from
TEDYDHFDY(SEQ ID NO: 72), SDDYDHFDY(SEQ ID NO: 73), SEEYDHFDY(SEQ ID NO: 74), SEDTDHFDY (SEQ ID NO: 75), SEDYEHFDY(SEQ ID NO: 76), SEDYDKFDY(SEQ ID NO: 77), SEDYDHWDY(SEQ ID NO: 78), SEDYDHFEY(SEQ ID NO: 79), SEDYDHFDT (SEQ ID NO: 80), SDEYDHFDY(SEQ ID NO: 81), SDEYDHFEY (SEQ ID NO: 82), TEDYEHFDY(SEQ ID NO: 83) or TDEYEHFDY(SEQ ID NO: 84).

The substantially homologous nucleic acid sequences also include nucleotide sequences that hybridize to the nucleic acid sequences disclosed (or their complementary sequences), e.g. hybridize to nucleotide sequences encoding one or more of the light chain or heavy chain CDRs of the invention, the light or heavy chain variable regions of the invention, or the binding proteins of the invention (or hybridize to their complementary sequences), under at least moderately stringent hybridization conditions, preferably under highly stringent hybridization conditions.

The term "substantially homologous" also includes modifications or chemical equivalents of the amino acid and nucleotide sequences of the present invention that perform substantially the same function as the proteins or nucleic acid molecules of the invention in substantially the same way. For example any substantially homologous binding protein should retain the ability to specifically bind to DLL4 and preferably to the same epitope thereof as recognized by the binding protein in question, for example, the same epitope or antigen recognised by the CDR domains of the invention or the $V_H$ and $V_L$ domains of the invention as described herein. Binding to the same epitope/antigen can be readily tested by methods well known and described in the art, e.g. using binding assays, e.g. a competition assay. Suitable non-genetically coded equivalents of the genetically amino acids are known in the art.

Substantially homologous sequences of proteins of the invention include, without limitation, conservative amino acid substitutions, or for example alterations which do not effect the $V_H$, $V_L$ or CDR domains of the binding proteins, e.g. include binding proteins where tag sequences or other components are added which do not contribute to the binding of antigen, or alterations to convert one type or format of antibody molecule or fragment to another type or format of antibody molecule or fragment (e.g. conversion from Fab to scFv or vice versa).

A "conservative amino acid substitution", as used herein, is one in which the amino acid residue is replaced with another amino acid residue having a similar side chain. Families of amino acid residues having similar side chains have been defined in the art, including basic side chains (e.g., lysine, arginine, histidine), acidic side chains (e.g. aspartic acid, glutamic acid), uncharged polar side chains (e.g. glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Homology may be assessed by any convenient method. However, for determining the degree of homology between sequences, computer programs that make multiple alignments of sequences are useful, for instance Clustal W (Thompson, J. D., D. G. Higgins, et al. (1994). "CLUSTAL W: Improving the sensitivity of progressive multiple sequence alignment through sequence weighting, position-specific gap penalties and weight matrix choice". Nucleic Acids Res 22: 4673-4680). If desired, the Clustal W algorithm can be used together with BLOSUM 62 scoring matrix (Henikoff S, and Henikoff J. G., 1992, Proc. Natl. Acad. Sci. USA 89: 10915-10919) and a gap opening penalty of 10 and gap extension penalty of 0.1, so that the highest order match is obtained between two sequences wherein at least 50% of the total length of one of the sequences is involved in the alignment. Generally, computer programs will be employed for such calculations. Programs that compare and align pairs of sequences, like ALIGN (E. Myers and W. Miller, "Optical Alignments in Linear Space", CABIOS (1988) 4: 11-17), FASTA (W. R. Pearson and D. J. Lipman (1988), "Improved tools for biological sequence analysis", PNAS 85:2444-2448, and W. R. Pearson (1990) "Rapid and sensitive sequence comparison with FASTP and FASTA" Methods in Enzymology 183:63-98) and gapped BLAST (Altschul, S. F., T. L. Madden, et al. (1997). "Gapped BLAST and PSI-BLAST: a new generation of protein database search programs". Nucleic Acids Res. 25: 3389-3402), BLASTP, BLASTN, or GCG (Devereux et al., Nucleic Acids Res., 1984, 12: 387) are also useful for this purpose. Furthermore, the Dali server at the European Bioinformatics institute offers structure-based alignments of protein sequences (Holm, J. of Mol. Biology, 1993, Vol. 233: 123-38; Holm, Trends in Biochemical Sciences, 1995, Vol 20: 478-480; Holm, Nucleic Acid Research, 1998, Vol. 26: 316-9).

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature. Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able readily to select appropriate hybridization conditions. In preferred embodiments, highly stringent hybridization conditions are selected. By way of example the following conditions may be employed to achieve highly stringent hybridization: hybridization at 5× sodium chloride/sodium citrate (SSC)/5×Denhardt's solution/1.0% SDS at Tm −5° C. based on the above equation, followed by a wash of 0.2×SSC/0.1% SDS at 60° C. Moderately stringent hybridization conditions include a washing step in 3×SSC at 42° C.

By way of further example, sequences which "hybridize" are those sequences binding (hybridising) under non-stringent conditions (e.g. 6×SSC, 50% formamide at room temperature) and washed under conditions of low stringency (e.g. 2×SSC, room temperature, more preferably 2×SSC, 42° C.) or conditions of higher stringency (e.g. 2×SSC, 65° C.) (where SSC=0.15M NaCl, 0.015M sodium citrate, pH 7.2).

It is understood, however, that equivalent stringencies may be achieved using alternative buffers, salts and temperatures. Additional guidance regarding hybridization conditions may be found e.g. in Sambrook et al., Molecular Cloning, a Laboratory Manual, Cold Spring Harbor Laboratory Press, 1989, Vol. 3.

The polypeptide, binding protein and nucleic acid molecules of the invention are preferably "isolated" molecules insofar as they are not present in situ within a human or animal body or a tissue sample derived from a human or animal body. The sequences may however correspond to, or be substantially homologous to, sequences as found in a human or animal body. Thus, the term "isolated" as used herein in reference to nucleic acid molecules, proteins or polypeptides refers to such molecules when isolated from or substantially free of their natural environment, e.g. isolated from the human or animal body (if indeed they occur naturally), or refers to such molecules when produced by a technical process, i.e. includes recombinant and synthetically produced molecules.

Thus, the term "isolated" may refer to a nucleic acid, protein or polypeptide substantially free of material with which it is naturally associated such as other nucleic acids or polypeptides and/or substantially free of cellular material or culture medium when produced by recombinant DNA techniques, or substantially free of chemical precursors, or other chemicals when chemically synthesized. An isolated nucleic acid may also be substantially free of sequences which naturally flank the nucleic acid (i.e. sequences located at the 5' and 3' ends of the nucleic acid) from which the nucleic acid is derived or sequences which have been made to flank the nucleic acid (e.g. tag sequences or other sequence which have no therapeutic value) by for example genetic engineering.

Isolated proteins may also be free of flanking sequences such as those described above for the isolated nucleic acid molecules.

The term "nucleic acid sequence" or "nucleic acid molecule" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid molecules may be double stranded or single stranded. The nucleic acid molecules may be wholly or partially synthetic or recombinant.

A person skilled in the art will appreciate that the proteins and polypeptides of the invention, such as the light and heavy complementarity determining regions, the light and heavy chain variable regions, binding proteins, antibodies and antibody fragments, and immunoconjugates, may be prepared in any of several ways well known and described in the art, but are most preferably prepared using recombinant methods.

Accordingly, the nucleic acid molecules of the present invention may be cloned or synthesised by any appropriate method and may be incorporated in a known manner into an appropriate expression vector which ensures good expression of the proteins of the invention. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which are operatively linked to the nucleic acid molecule. Operatively linked is intended to mean that the nucleic acid is linked to regulatory sequences in a manner which allows expression of the nucleic acid.

The invention therefore contemplates a recombinant expression vector containing a nucleic acid molecule of the invention, or a fragment thereof, and the necessary regulatory sequences for the transcription and translation of the protein sequence encoded by the nucleic acid molecule of the invention.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene which facilitates the selection of host cells transformed or transfected with a recombinant molecule of the invention. Examples of selectable marker genes are genes encoding a protein such as neomycin and hygromycin which confer resistance to certain drugs, β-galactosidase, chloramphenicol acetyltransferase or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein, provides increased solubility of the recombinant protein and/or aids in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors are known and include pGEX (Amrad Corp., Melbourne, Australia), which fuses, glutathione S-transferase (GST) to the recombinant protein.

In one embodiment, the recombinant expression vector contains a nucleic acid sequence which encodes a fusion moiety which provides a membrane anchor and a nucleic acid sequence which encodes a fusion moiety which provides a cell surface targeting signal. The binding protein of the invention may then be expressed as a fusion protein which is targeted to and retained at the cell membrane of the expression host cell. Suitable membrane anchor moieties are known in the art, but by way of example the PgsA anchor protein from *Bacillus subtilis* is mentioned here. Suitable cell surface targeting signals (secretion signals) are also known in the art. Such expression vectors may be used to express the binding proteins of the invention at the surface of the expression host cell, where they can interact with DLL4, preferably DLL4 expressed by said host cell.

In another embodiment, the recombinant expression vector contains a nucleic acid sequence which encodes a fusion moiety which provides a signal sequence which causes retention of the fusion protein in an intracellular compartment, e.g. the endoplasmic reticulum of the expression host cell. Suitable signal sequences are known in the art but the carboxy-terminal sequence HDEF is mentioned here by way of example. Such expression vectors may be used to express the binding proteins of the present invention in an intracellular compartment, where they can interact with DLL4 expressed by said host cell.

Thus, in a further aspect the present invention provides a method of gene therapy, wherein a recombinant expression vector as described herein is used to transform cells of a subject, wherein expression of the fusion protein prevents DLL4 from binding to its natural receptors and/or ligands, preferably Notch.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of eukaryotic host cells and prokaryotic cells. For example, the proteins of the invention may be expressed in yeast cells or mammalian cells. Other suitable host cells can be found in Goeddel, Gene Expression Technology: Methods in Enzymology 185, Academic Press, San Diego, Calif. (1991). In addition, the proteins of the invention may be expressed in prokaryotic cells, such as *Escherichia coli* (Zhang et al., Science 303(5656): 371-3 (2004)).

Yeast and fungi host cells suitable for carrying out the present invention include, but are not limited to *Saccharomyces cerevisiae* and the genus *Pichia*. Protocols for the transformation of yeast and fungi and suitable expression vectors are well known to those of ordinary skill in the art.

Mammalian cells suitable for carrying out the present invention include, among others HeLa cells (e.g. ATCC No. CCL 2).

Given the teachings provided herein, promoters, terminators, and methods, for introducing expression vectors of an appropriate type into plant, avian, and insect cells may also be readily accomplished.

Alternatively, the proteins of the invention may also be expressed in non-human transgenic animals such as rats, rabbits, sheep and pigs. In one embodiment, the proteins of the invention are expressed in humans.

The proteins of the invention may also be prepared by chemical synthesis using techniques well known in the chemistry of proteins such as solid phase synthesis.

N-terminal or C-terminal fusion proteins comprising the proteins of the invention conjugated with other molecules, such as proteins, may be prepared by fusion, through recombinant techniques. The resultant fusion proteins contain a protein of the invention fused to the selected protein or marker protein.

The proteins of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins which may be used to prepare fusion proteins or conjugates include cytotoxic polypeptides, radionucleotides, cytokines, antibody molecules, cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), truncated myc and any kind of enzymes. In a preferred embodiment, the binding proteins of the present invention are conjugated or fused with components of the T-cell receptor signalling system. This can endow an effector cell expressing the fusion protein with new specificities.

Accordingly, the invention provides a recombinant expression vector comprising one or more of the nucleic acid sequences of the invention or one or more of the nucleic acid sequences that encode the proteins of the invention (such as the light and heavy chain complementarity determining regions, the light and heavy chain variable regions, or the binding proteins, such as antibodies and antibody fragments).

Further, the invention provides a host cell comprising one or more of the recombinant expression vectors or one or more of the nucleic acid sequences of the invention, or a host cell expressing one or more of the proteins of the invention (such as the light and heavy chain complementarity determining regions, the light and heavy chain variable regions, or the binding proteins, such as antibodies and antibody fragments).

A yet further aspect of the invention provides a method of producing a protein of the present invention comprising a step of culturing the host cells of the invention. Preferred methods comprise the steps of (i) culturing a host cell comprising one or more of the recombinant expression vectors or one or more of the nucleic acid sequences of the invention under conditions suitable for the expression of the protein; and optionally (ii) isolating the protein from the host cell or from the growth medium/supernatant. Such methods of production may also comprise a step of purification of the protein product and/or formulating the product into a composition including at least one additional component, such as a pharmaceutically acceptable carrier or excipient.

In embodiments when the protein of the invention is made up of more than one polypeptide chain (e.g. certain fragments such as Fab fragments), then all the polypeptides are preferably expressed in the host cell, either from the same or a different expression vector, so that the complete proteins, e.g. binding proteins of the invention, can assemble in the host cell and be isolated therefrom.

The binding proteins of the invention have specificity for DLL4, which is expressed at the cell surface. Thus, the binding proteins of the invention can be used to detect DLL4-expressing cells or sites of aberrant DLL4 expression in vivo or in vitro. Thus, the binding proteins of the invention can target the body sites at which DLL4-expressing cells are present, whereupon the binding protein can act at the target site (e.g. target tissue, organ or cells).

Furthermore, the binding proteins of the invention can be conjugated to other entities and used to target these other entities to body sites at which DLL4-expressing cells are present. (Where the binding protein is an antibody molecule then such conjugates are also referred to as immunoconjugates).

Such other entities could be labels or other detectable moieties in which case these conjugate molecules would be useful for in vivo or in vitro diagnosis or imaging of body sites, in particular body sites afflicted with aberrant angiogenesis, e.g. cancer. Appropriate labels and detectable moieties are known in the art, but by way of example radionucleotides or paramagnetic particles are mentioned here. Detection can be carried out using known techniques, e.g. if the detectable moiety is a paramagnetic particle it can be detected using magnetic resonance imaging (MRI). If the detectable moiety is a radioactive substance, Positron emission tomography, also called PET imaging or a PET scan, may be used for imaging. Ultrasound or optical imaging may also be use where appropriate.

Alternatively, the binding proteins of the invention could be conjugated to biologically active molecules or medically relevant agents such as toxins, enzymes, drugs, pre drugs, pro drugs or other small molecule compounds, molecules that control coagulation such as Tissue factor, cytokines, or nucleic acid molecules, e.g. antisense molecules or viruses, in which case these conjugate molecules would be useful for targeted therapy, for example by targeting the drug, toxin or enzyme, etc., to cells or body sites at which DLL4-expressing cells, preferably carcinoma cells, are present. Such biologically active molecules or medically relevant agents may be in an active form or in a form which is to be activated, for example in the body. In particular, such molecules could be used for targeting DLL4-expressing cells, e.g. cancer cells. The skilled person will be well aware of examples of suitable molecules, e.g. suitable cytotoxic molecules. Examples of suitable molecules which may be conjugated to the binding proteins include saporin, ricin, gemcytabin and radionucleotides such as Samarium (commercially available under the name Quadramet™) pseudomonas exotoxin, diphtheria toxin, anthrax, tetanus toxin, abrin, capsicain and cromolyn.

Binding protein conjugates are thus preferred binding proteins of the invention. Preferred binding proteins to be used in the conjugates are full length (whole) antibodies, F(ab')$_2$, Fab or scFv.

Methods for conjugating such other entities to the binding proteins of the invention are well known and described in the art and an appropriate method can readily be selected depending on the nature of the binding protein and the other entity to be conjugated. Thus, the other entities can be conjugated to the binding proteins of the invention either directly or via an intermediate, e.g. an appropriate linker. The conjugation might for example be covalent or non-covalent (e.g. the other entities can be conjugated to the binding protein via the formation of a complex with the binding protein or more conveniently with an intermediate linking entity such as a chemical group or a peptide tag). Such binding as a complex is for example appropriate for many radioisotopes.

In such embodiments, the binding proteins (e.g. the antibody or antibody fragment), together with the conjugated entity, could be included or incorporated in an artificial membrane, forming e.g. an artificial particle such as a micelle, liposome, bubble or nanoparticle. These particles would be guided to a target body site by virtue of the binding protein and could then fuse with the cells at the target site or be internalised through the endosomal pathway, thereby releasing the conjugated entity, e.g. the biologically active molecules or medically relevant agents, from the inside of the artificial particle into the target cell, e.g. a tumour cell. Again, methods of incorporating molecules into such artificial membranes are well known and described in the art.

The present inventors investigated the expression of DLL4 in human pancreatic cancers and in normal pancreatic tissues. Immunostaining with a commercially available anti-human DLL4 mAb (R&D Systems Inc.) was performed to study the expression of DLL4 in clinical specimens of 10 pancreatic cancer cases as described in the Examples section. Sections of main tumour lesion containing lymph node metastasis were compared to sections of tumour-fee lesions, which may be considered to represent "normal" pancreatic tissue. In all cases, expression of DLL4 was highest in normal Langerhans' island and a substantial part of cancer cells, followed by small excretory duct, adipose tissue, small vessel, and the artery. Few, if any, positively stained cells could be seen in the main pancreatic duct and the mature vein. Within the vasculature, expression of DLL4 was relatively restricted to arteries and capillaries. In the artery, the predominant site of DLL4 expression was in or around the perithelium, but not the endothelium.

The skilled person will appreciate that the recombinant soluble form of DLL4 was used because it was readily available from commercial sources. The binding proteins of the present invention are capable of binding to native DLL4, so the present invention is not in any way limited to binding proteins against recombinant soluble DLL4.

The novel anti-DLL4 mAbs obtained in this manner reacted with CHO cells transfected with human DLL4, but not with mock-transfected (negative control) CHO cells, nor with CHO cells transfected with recombinant soluble murine DLL4, as shown in FIG. 1, showing that they have high specificity for human DLL4.

In addition, none of the three anti-DLL4 mAbs displayed any cross-reactivity with human Jagged1, Jagged2, or DLL1-transfected CHO cells (data not shown), further confirming their specificity for human DLL4.

The antibodies were also screened for their ability to block the binding of human Notch1-Fc to the DLL4 transfected CHO cells. The anti-DLL4 mAbs blocked the binding of Notch1-Fc to human DLL4-transfected CHO cells, as shown in FIG. 2.

The STL4 antibody was also screened for its ability to inhibit Notch-mediated signalling using a Notch/CSL reporter. The inhibitory effect of STL4 on Notch-mediated signalling is shown in FIG. 4.

The inventors have also demonstrated that the STL4 antibody has an inhibitory effect on the migration of HUVECs (Human Umbilical Vein Endothelial Cells) (see Example 7). Accordingly, the binding proteins can preferably modulate, e.g. inhibit or significantly reduce the chemotaxis of endothelial cells, preferably human endothelial cells, most preferably HUVEC cells.

Consequently, a further aspect of the invention provides the binding proteins of the invention as defined herein for use in therapy, diagnosis or imaging. Preferably, the binding proteins are for use in the treatment or diagnosis of a disorder or condition characterised by aberrant DLL4 signalling and/or aberrant angiogenesis. Alternatively viewed, the binding proteins are for use in modulating the level and/or function of DLL4. In one embodiment, the binding proteins are for use in modulating angiogenesis.

By "aberrant DLL4 signalling" is meant increased or decreased expression and/or activity of DLL4 and/or any of its ligands or receptors compared to the same tissue of a healthy individual at the same developmental stage. Preferably, aberrant DLL4 signalling means increased or decreased expression and/or activity of DLL4. Preferably, the expression and/or activity of DLL4 is increased.

Methods of determining expression levels are known in the art and include, but are not limited to, qualitative Western blot analysis, immunoprecipitation, radiological assays, polypeptide purification, spectrophotometric analysis, Coomassie staining of acrylamide gels, ELISA, rt-PCR, 2-D gel electrophoresis, microarray analysis, in situ hybridization, chemiluminescence, silver staining, enzymatic assays, ponceau S staining, immunohistochemical assays, radioimmunoassay, colorimetric analysis, immunoradiometric assays, positron emission tomography, Northern blotting, fluorometric assays and SAGE. See, for example, Ausubel et al, eds. (2002) Current Protocols in Molecular Biology, Wiley-Interscience, New York, By "angiogenesis" is meant the process of vascularization of a tissue involving the development of blood vessels, in particular capillary blood vessels. Angiogenesis may involve proliferation and/or differentiation of endothelial cells. Thus, angiogenesis encompasses the development, growth, extension, or persistence of a blood vessel.

By "aberrant angiogenesis" is intended any disorder, disease, or developmental condition that involves atypical development, growth, extension, or persistence of a blood vessel such as, but not limited to, a capillary blood vessel.

By "modulating the level of DLL4" is intended a change of at least 1%, 5%, preferably at least 10%, 20%, more preferably at least 30%, 40%, 50%, 60%, 70%, 80%, 90%, 99% in the level of DLL4 present in a target area or tissue.

By "modulating angiogenesis" is intended a change of at least 1%, 5%, preferably at least 10%, 20%, more preferably at least 30%, 40%, 50%, 60%, 70%, 80%, 90%, 99% in the volume or number of vascular endothelial cells and/or in the density of blood vessels in a target area or tissue.

The ability of a binding protein to modulate angiogenesis may be assayed using techniques well known in the art. For example, an HUVEC (human umbilical vein endothelial cell) fibrin gel bead assay may be used to investigate proliferation and the formation of sprouts with a distinct lumen-like structure. Vascular density may be quantified by immunohistochemical staining with a suitable antibody, e.g. an endothelial-cell specific antibody. Briefly, tissue samples are first contacted with a suitable primary antibody and then with an appropriate labelled secondary antibody. The secondary antibody is visualised and the signal location and intensity is scored. A skinfold chamber model may be used to monitor angiogenesis in vivo.

Preferably, the disorder or condition is selected from atherosclerosis, arthritis, ocular neovascularisation, endometriosis, uterine fibroids, pre-eclampsia and cancer, cancer being especially preferred. In embodiments where cancer is treated, the cancer is preferably selected from cervical cancer, uterine cancer, ovarian cancer, pancreatic cancer, kidney cancer, gallbladder cancer; liver cancer, head and neck cancer, squamous cell carcinoma, gastrointestinal cancer, breast cancer (such as carcinoma, ductal, lobular, and nipple), prostate cancer, testicular cancer, lung cancer, non-small cell lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer (e.g. astrocytoma, glioblastoma, medulloblastoma), neuroblastoma, sarcomas, colon cancer, rectum cancer, stomach cancer, anal cancer, renal cancer, bladder cancer, pancreatic cancer, endometrial cancer, plasmacytoma, lymphomas, retinoblastoma, Kaposi's sarcoma, Wilm's tumour, Ewing sarcoma, melanoma and other skin cancers. Preferably, the cancer is prostate or pancreatic cancer. In an especially preferred embodiment, solid tumours are treated. In another preferred embodiment, metastasis is prevented.

A further aspect of the invention provides the binding proteins of the invention as defined herein for use in a method of contraception. The corpus luteum (CL) is a site of intense angiogenesis, the formation of a dense capillary network enabling the hormone-producing cells to obtain the oxygen, nutrients and hormone precursors necessary to synthesise and release large amounts of progesterone required for establishment and maintenance of early pregnancy. This opens up the possibility of using the binding proteins of the present invention as a contraceptive.

A further aspect of the invention provides the binding proteins of the invention as defined herein for use in reducing or preventing aberrant angiogenesis after transplantation. High levels of angiogenesis at the transplantation site may be problematic, so it may be desirable to control the level of angiogenesis, and in some cases, e.g. when a cornea or part thereof is transplanted, it is desired to keep angiogenesis at the transplantation site to a minimum. The present invention therefore provides a method of improving the outcome of transplantation therapy, which method comprises administration of a suitable amount of a binding protein or expression vector as hereinbefore described to a patient before, during and/or after transplantation has been carried out. There is also provided a method of in vitro treatment of a transplant with a suitable amount of a binding protein of the invention prior to transplantation, to reduce angiogenesis after transplantation.

In addition, the invention provides compositions comprising the binding proteins of the invention, such as antibodies and antibody fragments, and/or expression vectors of the present invention, with one or more pharmaceutically acceptable excipient, carrier, diluent, buffer or stabilizer.

Such compositions can be used in any of aspects of the invention described herein where a binding protein or expression vector is used, e.g. can be used in any of the methods, uses or kits as described herein.

A yet further aspect of the invention provides the use of the binding proteins and/or expression vectors of the invention as defined herein in the manufacture of a composition or medicament for use in any therapy or diagnostic technique described herein.

Methods of treatment of a subject comprising the administration of an effective amount of a binding protein of the invention as defined herein to a subject, or to a sample (e.g. a blood sample) removed from a subject and which is subsequently returned to the subject, provide yet further aspects of the invention.

The in vivo methods as described herein are generally carried out in a mammal. Any mammal may be treated, for example humans and any livestock, domestic or laboratory animal. Specific examples include mice, rats, pigs, cats, dogs, sheep, rabbits, cows and monkeys. Preferably however the mammal is a human.

The terms "therapy" or "treatment" as used herein include prophylactic therapy, which may result in the prevention of disease. The terms "therapy" and "treatment" include combating or cure of disease but also include the controlling, reduction or alleviation of disease or one or more of the symptoms associated therewith.

An "effective amount" as used herein can refer to a therapeutically effective amount or a prophylactically effective amount depending on the nature of the treatment, or an amount effective for contraception, diagnosis or imaging. A therapeutically effective amount can be considered to be an amount necessary (at appropriate dosages and administration regimes) to achieve the desired therapeutic result. A prophylactically effective amount can be considered to be an amount necessary (at appropriate dosages and administration regimes) to achieve the desired prophylactic result. As indicated below, the amounts are likely to vary depending on the weight, age and sex of the patient, the severity of the disease and the ability of the binding protein to elicit a desired response in the individual.

The compositions of the present invention can be formulated according to any of the conventional methods known in the art and widely described in the literature. Thus, the active ingredient (i.e. the binding protein) may be incorporated, optionally together with other active substances (examples of which are as described below), with one or more conventional pharmaceutically acceptable carriers, diluents and/or excipients, etc., appropriate for the particular use for a composition, to produce conventional preparations which are suitable or can be made suitable for administration. They may be formulated as liquids, as semi-solids or as solids, e.g. liquid solutions, dispersions, suspensions, tablets, pills, powders, sachets, cachets, elixirs, emulsions, syrups, ointments, liposomes, suppositories, and the like. The preferred form depends on the intended mode of administration and therapeutic application. Preferably the composition comprising the binding protein of the invention is prepared in a form of an injectable or infusible solution.

The preferred mode of administration is parenteral, e.g. intraperitoneal, intravenous, subcutaneous, intramuscular, intracavity or transdermal, although any other appropriate mode may be used, for example oral administration. Intravenous injection or infusion is especially preferred. Any appropriate site of administration may be used. For example they may be administered locally and directly at the site where action is required or may be attached or otherwise associated, e.g. conjugated, with entities which will facilitate the targeting to an appropriate location in the body.

Any physiologically compatible carrier, excipient, diluent, buffer or stabilizer can be used in the compositions of the invention. Examples of suitable carriers, excipients, diluents, buffers and stabilizers include one or more of water, saline, phosphate buffered saline, dextrose, glycerol, ethanol and the like, as well as combinations thereof. In some cases isotonic agents, e.g. sugars, polyalcohols (e.g. mannitol, sorbitol), or sodium chloride may be included. The compositions may additionally include lubricating agents, wetting agents, emulsifying agents, suspending agents, preserving agents, sweetening agents, flavouring agents, and the like. The compositions of the invention may be formulated so as to provide quick, sustained or delayed release of the active ingredient after administration to the subject by employing procedures well known in the art. As described above, preferably the composition is in a form suitable for injection and suitable carriers may be present at any appropriate concentration, but exemplary concentrations are from 1% to 20% and preferably from 5% to 10%.

Therapeutic compositions typically must be sterile and stable under conditions of manufacture and storage. Appropriate ways of achieving such sterility and stability are well known and described in the art.

In addition to a binding protein of the invention, the composition may further comprise one or more other active ingredients such as other agents which are useful for treating diseases with which aberrant DLL4 signalling is associated or in which DLL4 activity is detrimental, e.g. cancers, atherosclerosis, arthritis or ocular neovascularization. Suitable additional active agents for inclusion in a composition that is to be used in the treatment of mammals will be known to a person skilled in the art and can be selected depending on the nature of the disease which is to be treated by the composition. Suitable additional agents for the treatment of cancer include antibodies which bind to other targets, cytokines, and chemical agents, e.g. standard chemotherapeutics (small molecule drugs) or drugs controlling side effects.

Suitable doses of the binding protein of the invention and the other active ingredients (if included) will vary from patient to patient and will also depend on the nature of the particular disease. Preferably, said dosages constitute a therapeutically effective amount or a prophylactically effective amount, depending on the nature of the treatment involved. Suitable doses can be determined by the person skilled in the art or the physician in accordance with the weight, age and sex of the patient and the severity of the disease. The ability of the binding protein to elicit a desired response in the individual will also be a factor. Exemplary daily doses are: 0.1 to 250 mg/kg, preferably 0.1 to 200 or 100 mg/kg, more preferably 1 to 50 or 1 to 10 mg/kg, e.g. about 5 mg/kg of the active ingredient. This can be administered as a single unit dose or as multiple unit doses administered more than once a day. It is to be noted however that appropriate dosages may vary depending on the patient and that for any particular subject, specific dosage regimes should be adjusted over time according to the individual needs of the patient. Thus, the dosage ranges set forth herein are to be regarded as exemplary and are not intended to limit the scope or practice of the claimed composition.

The invention further includes kits comprising one or more of the binding proteins or compositions of the invention and/or one or more of the nucleic acid molecules encoding the binding proteins of the invention, and/or one or more recombinant expression vectors comprising the nucleic acid sequences of the invention, and/or one or more host cells comprising the recombinant expression vectors or nucleic acid sequences of the invention. Preferably said kits are for use in the methods and uses as described herein. Preferably said kits comprise instructions for use of the kit components.

The binding proteins as defined herein may also be used as molecular tools for in vitro or in vivo applications and assays. As the binding proteins have an antigen binding site, these can function as members of specific binding pairs and these molecules can be used in any assay where the particular binding pair member is required. For example, in the embodiments when the binding proteins are antibodies or antibody fragments which can bind particular antigens such as DLL4, these molecules can be used in any assay requiring an antibody with a specificity for that particular antigen, for example they can be used in any assay where detection of DLL4 is required or desired. Diagnostic methods and uses involving the binding proteins disclosed herein comprise a further aspect of the invention.

A further aspect of the invention is therefore a method of diagnosis or imaging of a subject comprising the administration of an appropriate amount of a binding protein (e.g. binding protein conjugate) of the invention as defined herein to the subject and detecting the presence and/or amount and/or the location of the binding protein or binding protein conjugate of the invention in the subject.

In a further aspect, the binding proteins of the invention may be used to modulate angiogenesis in vitro.

Accordingly, the invention includes the use of the binding proteins of the invention to modulate the activity of DLL4 and/or Notch in vitro. For example, the binding proteins of the invention can be used to interfere with or inhibit DLL4 and/or Notch activity.

The binding proteins of the invention may also be used to produce further binding proteins which are specific for DLL4. Such uses involve for example the addition, deletion, substitution or insertion of one or more amino acids in the amino acid sequence of a parent binding protein to form a new binding protein, wherein said parent binding protein is one of the binding proteins of the invention as defined elsewhere herein, and testing the resulting new binding protein to identify binding proteins specific for DLL4. Such methods can be used to form multiple new binding proteins which can all be tested for their ability to bind DLL4. Preferably said addition, deletion, substitution or insertion of one or more amino acids takes place in one or more of the CDR domains.

Such modification or mutation to a parent binding protein can be carried out in any appropriate manner using techniques well known and documented in the art, for example by carrying out methods of random or directed mutagenesis. If directed mutagenesis is to be used then one strategy to identify appropriate residues for mutagenesis utilizes the resolution of the crystal structure of the binding protein-antigen complex, e.g. the antibody-antigen complex, to identify the key residues involved in the antigen binding (Davies D. R., Cohen G. H. 1996. Interactions of protein antigens with antibodies. Proc Natl. Acad. Sci. U.S.A. 93, 7-12). Subsequently, those residues can be mutated to enhance the interaction. Alternatively, one or more amino acid residues can simply be targeted for directed mutagenesis and the effect on binding to DLL4 assessed.

Random mutagenesis can be carried out in any appropriate way, e.g. by error-prone PCR, chain shuffling or mutator *E. coli* strains.

Thus, one or more of the $V_H$ domains of the invention can be combined with a single $V_L$ domain or a repertoire of $V_L$ domains from any appropriate source and the resulting new binding proteins tested to identify binding proteins specific for DLL4. Conversely, one or more of the $V_L$ domains of the invention can be combined with a single $V_H$ domain or repertoire of $V_H$ domains from any appropriate source and the resulting new binding proteins tested to identify binding proteins specific for DLL4.

Similarly, one or more, or preferably all three CDRs of the $V_H$ and/or $V_L$ domains of the invention can be grafted into a single $V_H$ and/or $V_L$ domain or a repertoire of $V_H$ and/or $V_L$ domains, as appropriate, and the resulting new binding proteins tested to identify binding proteins specific for DLL4.

The targeted mutations of the CDRs, especially may be an effective technique for increasing antibody affinity and are preferred. Preferably, blocks of 3 to 4 amino acids of the CDR3 are targeted for mutagenesis.

Preferred target sites for mutation are those that code for exposed amino acids and preferably those that encode amino acids which form part of the antigen binding sites. Other preferred target sites for mutation are those that code for non-conserved amino acids.

Methods of carrying out the above described manipulation of amino acids and protein domains are well known to a person skilled in the art. For example, said manipulations could conveniently be carried out by genetic engineering at the nucleic acid level wherein nucleic acid molecules encoding appropriate, binding proteins and domains thereof are modified such that the amino acid, sequence of the resulting expressed protein is in turn modified in the appropriate way.

Testing the ability of one or more new binding proteins to specifically bind to DLL4 can be carried out by any appropriate method which are well known and described in the art. Recombinant soluble human DLL4 is commercially available (see the Examples) and this can readily be used to assay binding, for example by conventional methods such as ELISA, affinity chromatography, etc.

The new binding proteins produced by these methods will preferably have at least an equivalent affininity for DLL4 as the parent binding protein and can be treated and used in the same way as the binding proteins of the invention as described elsewhere herein (e.g. for therapy, in compositions etc). In some embodiments the new binding proteins have a lower affinity for DLL4 than the parent binding protein.

New binding proteins produced, obtained or obtainable by these methods form a yet further aspect of the invention.

Other features and advantages of the present invention will become apparent from the above detailed description. It should be understood, however, that the above detailed description and the following specific examples, while indicating preferred embodiments of the invention, are given by way of illustration only, since various changes and modifications within the spirit and scope of the invention will become apparent to those skilled in the art from the detailed description.

The invention will now be described in more detail in the following non-limited examples with reference to the drawings in which:

FIG. 1

Shows the characterisation of the novel anti-DLL4 antibody of the present invention by flow cytometry. Flow cytometry was used to assay the binding of a novel antibody to Chinese hamster ovary (CHO) cells transfected with murine DLL4 (FIG. 1 a) mock-transfected (null control, FIG. 1 b) or transfected with human DLL4 (FIG. 1 c).

The cells were incubated with a biotinylated novel anti-DLL4 antibody and with a biotinylated mouse IgG1, the mouse IgG1 serving as a control. The cells were then incubated with PE-labelled streptavidin. The bold histogram shows cells labelled with the anti-DLL4 antibody and the thinner histogram shows the cells labelled with the mouse IgG1.

FIG. 2

Shows the characterisation of the novel anti-DLL4 antibody of the present invention by flow cytometry. Chinese hamster ovary (CHO) cells transfected with human DLL4 were pre-incubated with control mouse IgG1 (thin histogram) or with the anti-DLL4 antibody of the present invention (bold histogram) and then stained with Notch1-Fc followed by biotinylated anti-human IgG1 mAB and PE-labelled streptavidin. The dotted histogram shows the background staining with biotinylated anti-human IgG1 mAB and PE-labelled streptavidin.

FIG. 3

Is a graph showing the effect of an anti-DLL4 antibody prepared by the inventors on tumor volume (see Example 4). The y-axis shows the tumor volume in $mm^3$ and the x-axis shows time in days.

FIG. 4 is a graph which summarises the results of the Notch signalling assay of Example 6. The Y-axis indicates light units measured by a luminometer. The light units are an indirect measure of notch-dependent gene transcription. The x-axis shows from left to right:
a) the base level of light (luciferase transcription) in the absence of any added Dll4 or anti-Dll4-antibody
b) the effect of adding the STL4 antibody in the absence of added DLL4
c) the level of light (luciferase transcription) in the presence of added Dll4 (without antibody)
d) the effect of adding the STL4 antibody in the presence of added Dll4.

FIG. 5 is a graph which summarises the results of the HUVEC migration assay of Example 7. The number of migrated cells are shown on the Y-axis and the x-axis shows from left to right:
a) 5% fetal calf serum (FCS)
b) no FCS
c) and d) FCS and STL4
e) and f) preincubated with STL4, then FCS All assays were carried out using cells under normal oxygen conditions (grey bars) and cells under hypoxic conditions (black bars).

EXAMPLES

Materials and Methods

Figure 1:
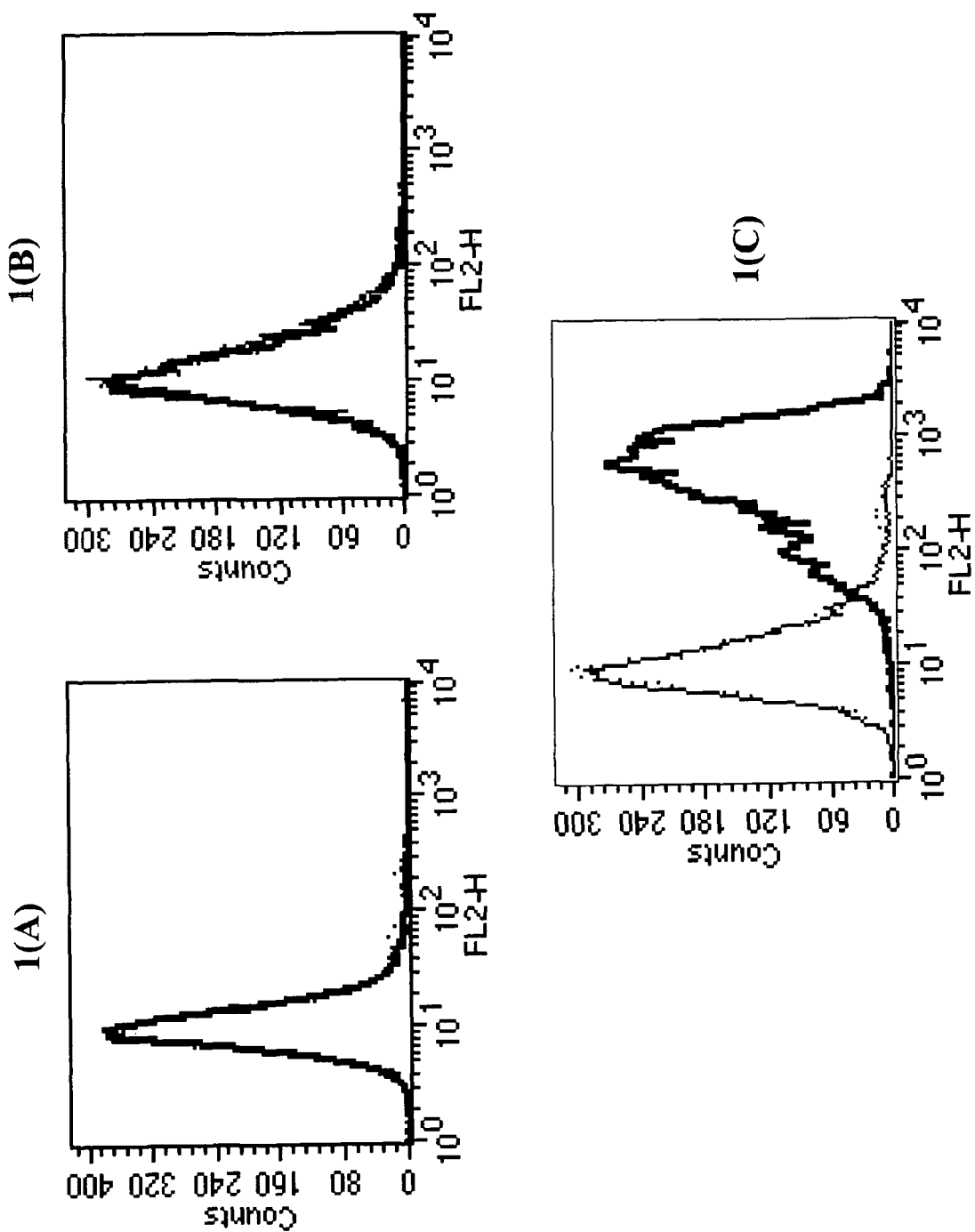

Cells and Culture Conditions.

A PK-1 human pancreatic adenocarcinoma cell line, established as previously described (Kobari M. Establishment of a human pancreatic cancer cell line and detection of pancreatic cancer associated antigen. Tohoku J. Exp. Med., 143: 33-46, 1984), and other pancreatic cancer cell lines were maintained in RPMI 1640 supplemented with 10% foetal calf serum (FCS), 100 units/ml penicillin, and 0.1 mg/ml streptomycin in a humidified 5% $CO_2$ atmosphere at 37° C. Immortalized normal human pancreatic duct cell line, kindly provided by Dr. Furukawa (Department of pathology, Tohoku University School of Medicine, Sendai, Japan), HEK 293 cell, fibroblasts, and endothelial cell lines were cultured in low glucose DMEM containing 10% FCS, and were maintained in the same conditions as cancer cell lines. Cells were not used beyond passage 6.

CHO cells were transfected with plasmids encoding either murine Dll4, human Dll4 or a control (empty) plasmid. Stable cell lines were selected and cloned.

Animals

Male SCID mice (6-8-week-old) were purchased from Nippon Clea Co. (Tokyo, Japan) or Charles River Co. (Tokyo, Japan), kept in specific pathogen-free environment and allowed free access to food and water. The NIH guidelines for the care and treatment of the animals were followed.

Statistical Analysis.

All of the experiments were performed in duplicate or triplicate. Representative data from each experiment is presented (mean values±SD or SE). Two-tailed Student's t test was used for the statistical analysis. Values of $P \leq 0.05$ were considered significant.

Example 1

Clinical Specimen and Immunohistochemical Staining.

Ten specimens of human pancreatic cancer had been obtained by surgery. All patients gave signed informed consent for their tissues to be used for scientific research. The normal and tumour regions were identified. Human tissue samples were fixed in 10% formalin at 4° C., embedded in paraffin, and stored at 4° C. Sections (5 μm) were cut individually for immunohistochemical staining. Paraffin sections were de-paraffinized in xylene for 5 minutes, treated with a graded series of alcohol [100%, 95%, and 80% ethanol/double-distilled $H_2O$ (v/v)], and rehydrated in PBS three times for 5 minutes each time.

After blocking endogenous peroxidase activity by incubating the slides in 0.3% $H_2O_2$ solution in 30% methanol for 15 minutes, antigen reactivity was gained by treating with the antigen retrieval agent (Pharmingen, Retrivagen A) for 10 minutes at 89° C. in a microwave. The sections were incubated with the appropriate primary antibody (diluted in PBS containing 1% FBS) in humidified chamber overnight at 4° C., and rinsed with PBS three times for 5 minutes each time. Sections were then incubated for 60 minutes with the appropriate secondary antibody at room temperature.

Expression of human DLL4 was detected using a rat mAb (R&D Systems) as the primary Ab and biotinylated anti-rat IgG antibody (R&D Systems) as the secondary Ab. After incubation with peroxidase-labelled streptoavidin at room temperature for 30 minutes, positive reactions were visualized by incubating the slides with 3,3'-diaminobenzidine for 5 to 15 minutes. The reactions were terminated by rinsing the slides with distilled water. The slides were counterstained with hematoxylin, mounted with Universal Mount, and dried at room temperature.

Results—Expression of DLL4 in Pancreatic Cancers.

Sections of main tumour lesion containing lymph node metastasis, as well as sections of lesions free from tumour ("normal" pancreatic tissue) were stained as described above. In all cases, expression of DLL4 was highest in normal Langerhans' island and a substantial part of cancer cells, followed by small excretory duct, adipose tissue, small vessel, and the artery. Few, if any, positively stained cells could be seen in the main pancreatic duct and the mature vein. Within the vasculature, expression of DLL4 was relatively restricted to arteries and capillaries. In the artery, the predominant site of DLL4 expression was pericular side, but not endothelium.

Example 2

Generation of Neutralizing mAbs Against Human DLL4.

Neutralizing mAbs against human DLL4 were generated by immunizing a BALB/c mouse with recombinant soluble human DLL4 (R&D Systems). The immune splenocytes were fused with P3U1 myeloma and reactivity of the antibodies to CHO (Chinese hamster ovary) cells transfected with mouse DLL4 or human DLL4 was assayed by flow cytometry. Antibodies which displayed positive results with human but not murine DLL4 were purified from ascites generated in pristan-primed nude mice by the caprylic acid/ammonium sulfate precipitation method.

Example 3

Characterization of Neutralizing mAbs Against Human DLL4.

Figure 2:
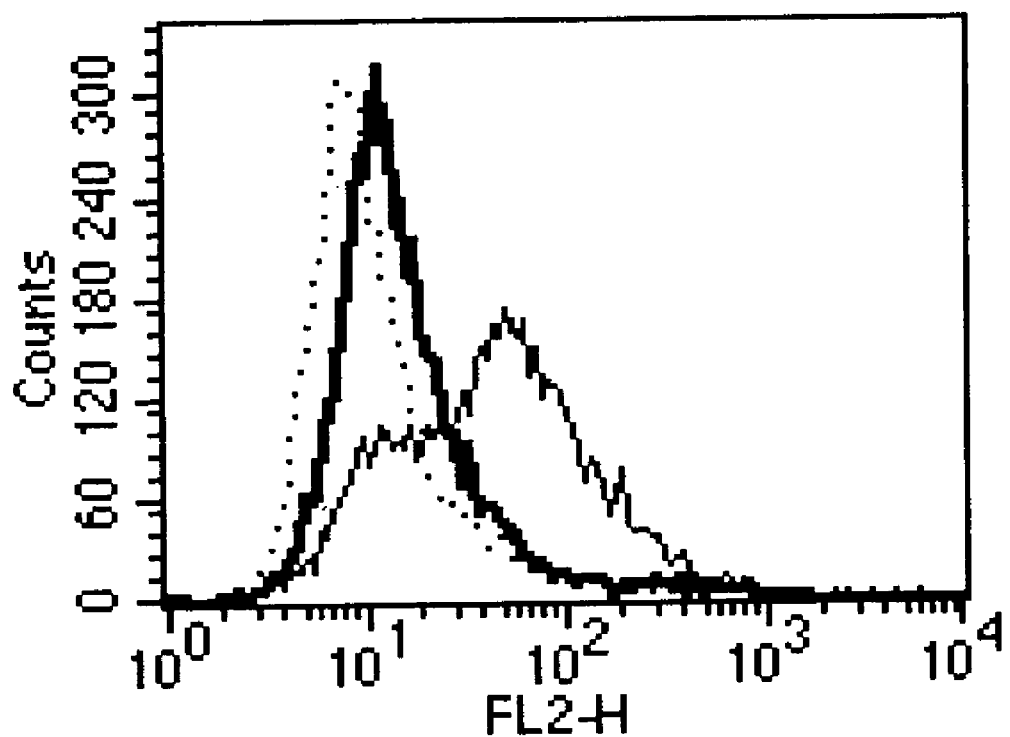

Three new neutralizing mAbs against human DLL4 were generated as described in Example 2'. All three anti-human DLL4 mAbs reacted with human DLL4-transfected CHO cells but not with mock-transfected or mouse DLL4-transfected CHO cells (exemplified with one antibody in FIG. 1). In addition, none of the three anti DLL4 mAbs cross-reacted with human Jagged1, Jagged2, or DLL1-transfected CHO cells (data not shown). All three anti DLL4 mAbs blocked the binding of Notch1-Fc to human DLL4-transfected CHO cells (exemplified one antibody in FIG. 2). These data indicate that the novel antibodies react with an epitope close to or overlapping the Notch binding site on Dll4.

One of these antibodies, termed STL4, was selected for further characterisation, based on stronger reactivity with DLL4 in a dilution series of culture supernatant.

Example 4

Effect of anti-DLL4 Antibodies on Tumour Growth

PK-1 cells ($1 \times 10^7$/100 μl RPMI) were injected subcutaneously into the dorsal flank area of the mice. This causes the growth of a tumour consisting of human cells within the mouse. One week after the inoculation, they were randomized into groups of 10 mice each. One group received a treatment with monoclonal antibody raised against human DLL4. The other group severed as a negative control, receiving control hamster IgG (Jackson ImmunoResearch).

The treatment consisted of intra-peritoneal injection twice weekly for five weeks. The tumour diameter was measured twice a week using a caliper, and tumor volume was determined by the formula: $V=D \times d^2 \times 0.4$, where V=tumour volume, D=biggest diameter, and d=smallest diameter.

Figure 3:
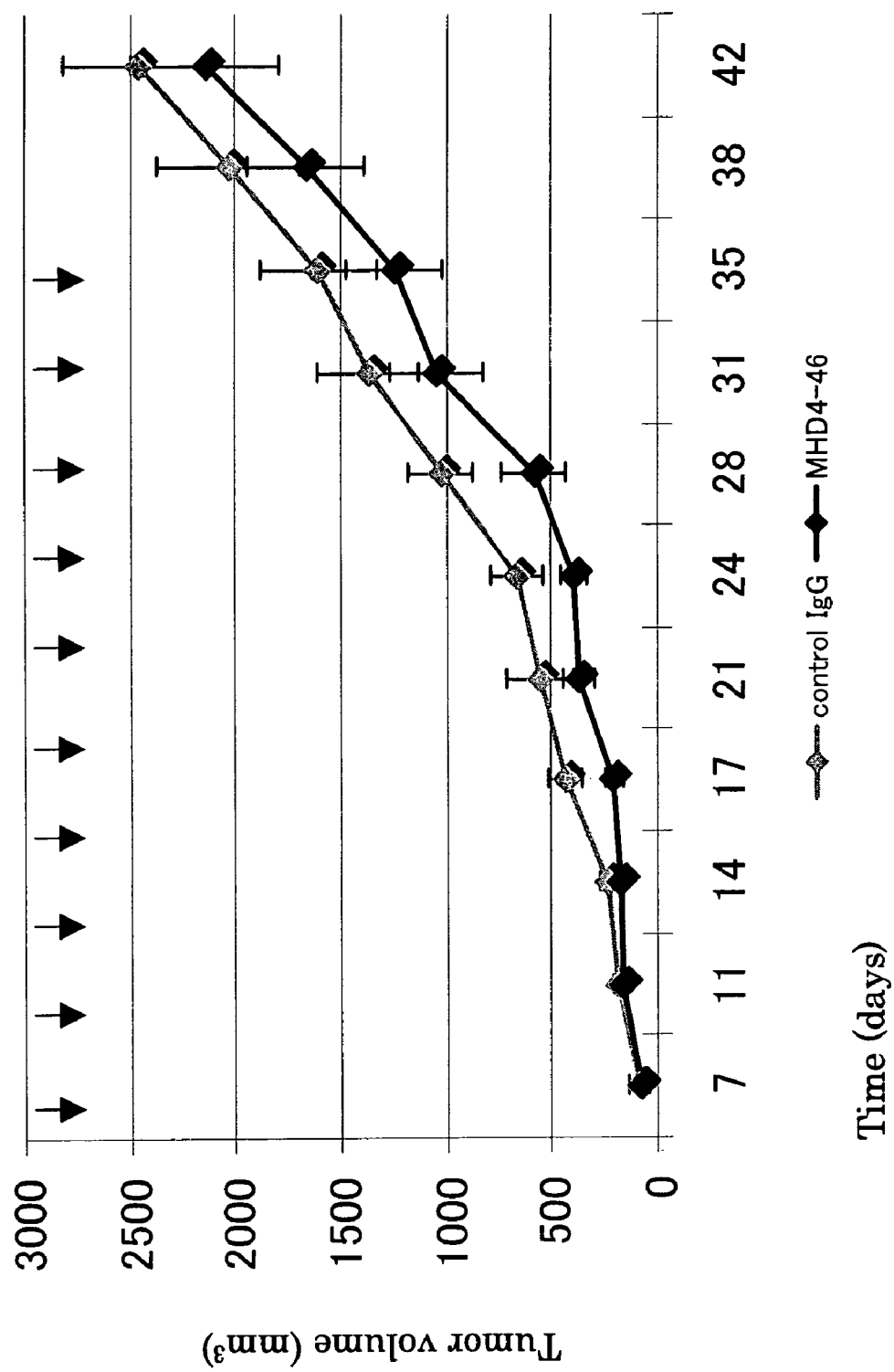

Results are shown in FIG. 3. It can be seen that the anti-human DLL4 antibody caused inhibition of tumour growth.

This experiment was carried out in a mouse model, so angiogenesis was largely modulated by murine DLL4 and the anti-human DLL4 could clearly not inhibit murine DLL4 (as shown in Example above). In a human subject all DLL4 is human, so the anti-DLL4 antibody can be expected to give even better results.

These data highlight the importance of vascular-derived Dll4 in the control of tumour angiogenesis.

In this animal model an effective dose of the anti-Dll4-antibody (STL4) showed no toxic effects.

Example 5

Expression of DLL4 on Human Cells and Tissue

DLL4 has previously been shown to be expressed on a range of human tumour cells. The reactivity of STL4 was tested using flow cytometry analysis on a range of human cell lines derived from breast carcinomas and immunohistochemistry analysis on pancreatic tumour samples, prostate tumour samples or human bladder carcinoma samples. STL4 reactivity was demonstrated in all of these samples.

Example 6

Notch Signalling Assay

This assay was carried out in order to determine if STL4 can interfere in DLL4 mediated Notch signalling.

Plates were coated with a filter-sterilised 0.2% gelatin solution (over night) either with or without the addition of recombinant DLL4 ligand at 1 µg/mL. HEK293a cells (which express Notch) were then seeded onto these plates. The following day the cells were transfected with the Notch/CSL reporter. The Notch/CSL reporter contains a promoter harbouring multiple CBF-1 DNA binding sites to which endogenous CBF-1 will bind and represses gene transcription. Subsequent to binding of Notch ligands (e.g. DLL4) to Notch receptors, cleavage of the Notch receptor will occur, leading to the release of the Notch intracellular domain, which then binds to CBF-1 and transforms it from a repressor into an activator of transcription, driving the luciferase reporter molecule. One hour later appropriate wells had STL4 added to them at 125 µl/mL. The next day the whole plate was read using the ONE GLO reagent to measure luciferase activity, and the plates read in a luminometer.

Figure 4:
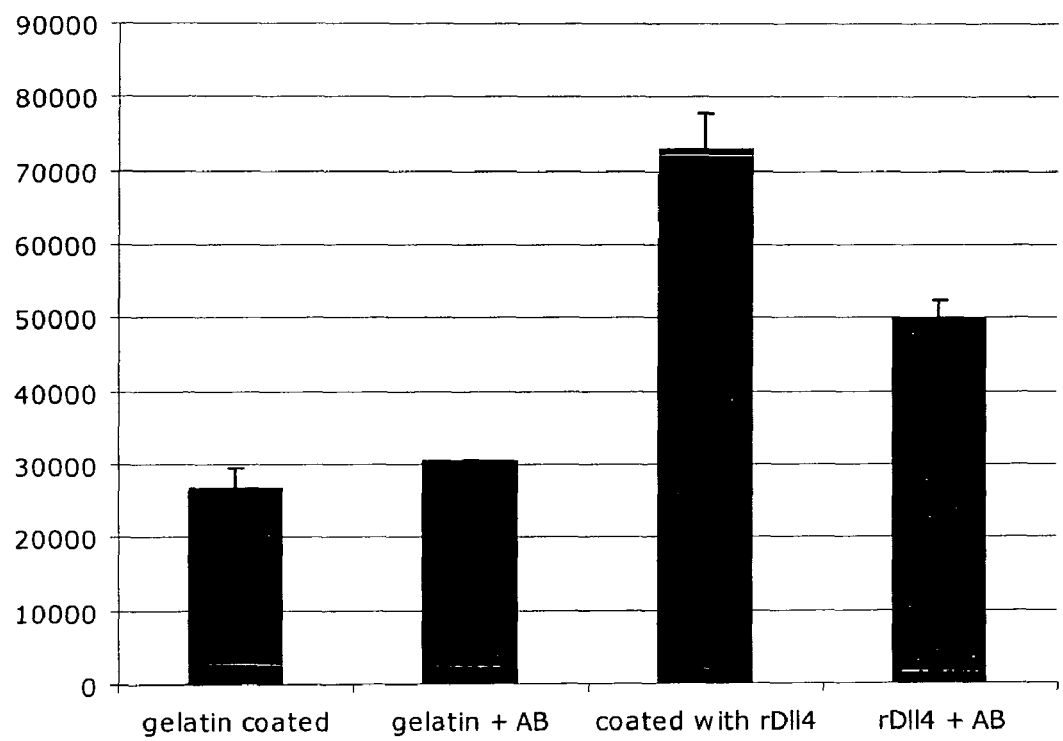

The results are shown in FIG. 4. As can be seen from this Figure, HEK293 cells showed activation of the Notch signalling cascade on wells coated with DLL4, but not on control wells. This signalling was blocked by STL4. An isotype control antibody had no effect on the DLL4-mediated activation of Notch (data not shown). These data indicate that STL4 blocks DLL4 interaction with Notch and so can interfere with Notch mediated signalling.

Example 7

HUVEC Migration Assay

HUVEC (purchased from TCS CellWorks, Claydon, UK) were cultured in Large Vessel Endothelial Cell Growth Medium. CellTracker Green dye CMFDA (purchased from Molecular Probes) was added to cell culture flask medium to give a 5 µM final concentration of dye and left in incubator for 1 hour. Cells were trypsinised and counted.

To the transwell insert (3 µm pore BD FluoroBlok purchased from BD Biosciences), cells at the dilution of $3 \times 10^4$ in 300 µl were added. To the bottom of the well 800 µl of serum free medium containing chemoattractant (5% FCS) was added. Cells were left to migrate for 4 hours. Cells that migrated were viewed under UV illumination in real time. Migration data was processed using Image Pro Plus Software (MediaCybernetics UK)

Results

Figure 5:
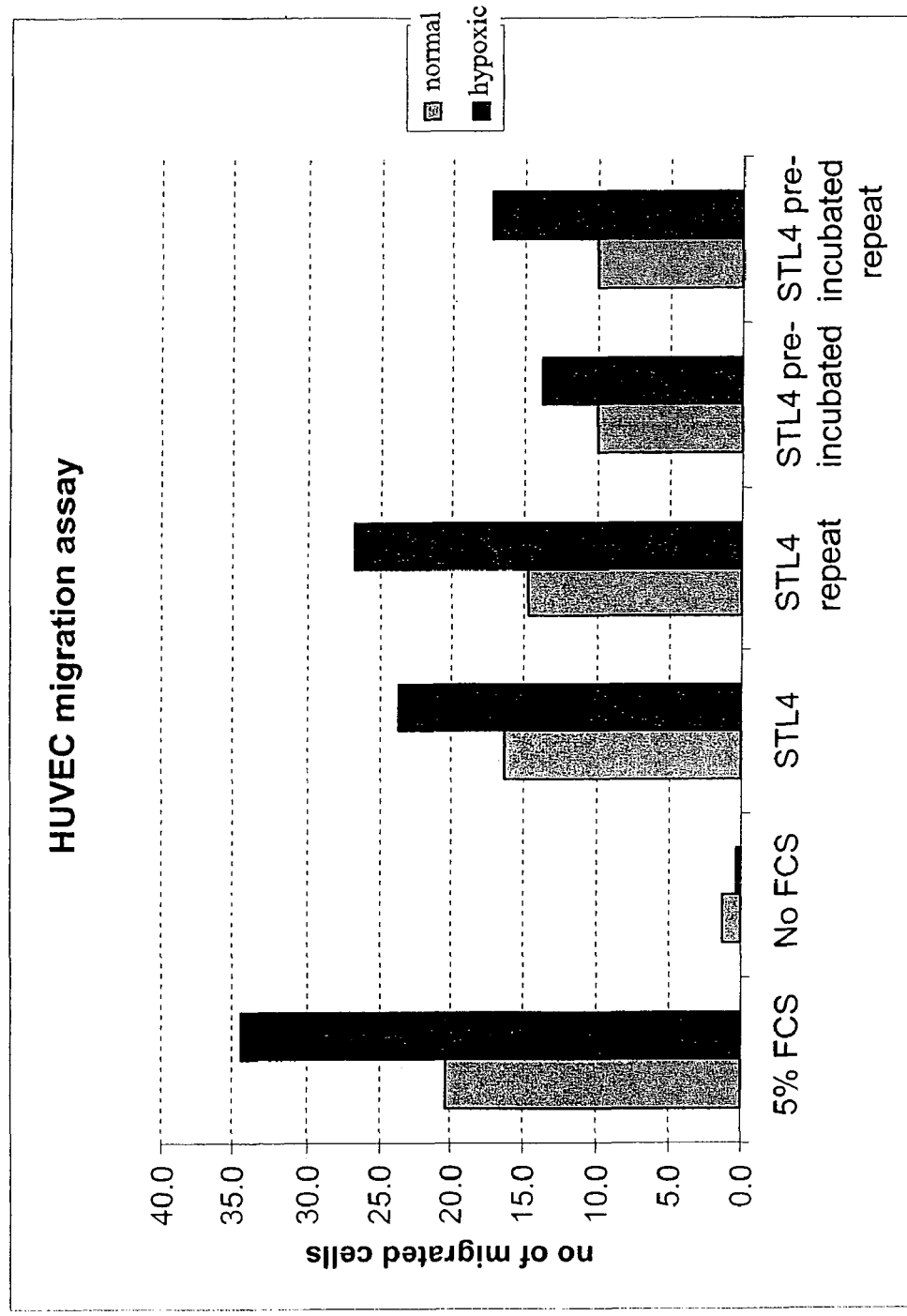

Addition of STL4 to cultures of human endothelial cells had no significant effect on the growth of these cells (data not shown). However, when used in the migration assay, STL4 was capable of blocking the migration of HUVECs towards FCS in both normoxic and hypoxic conditions (FIG. 5). These data indicate that STL4 is capable of interfering with angiogenesis.

Example 8

Preparation of a Chimeric Antibody

Figure 6:
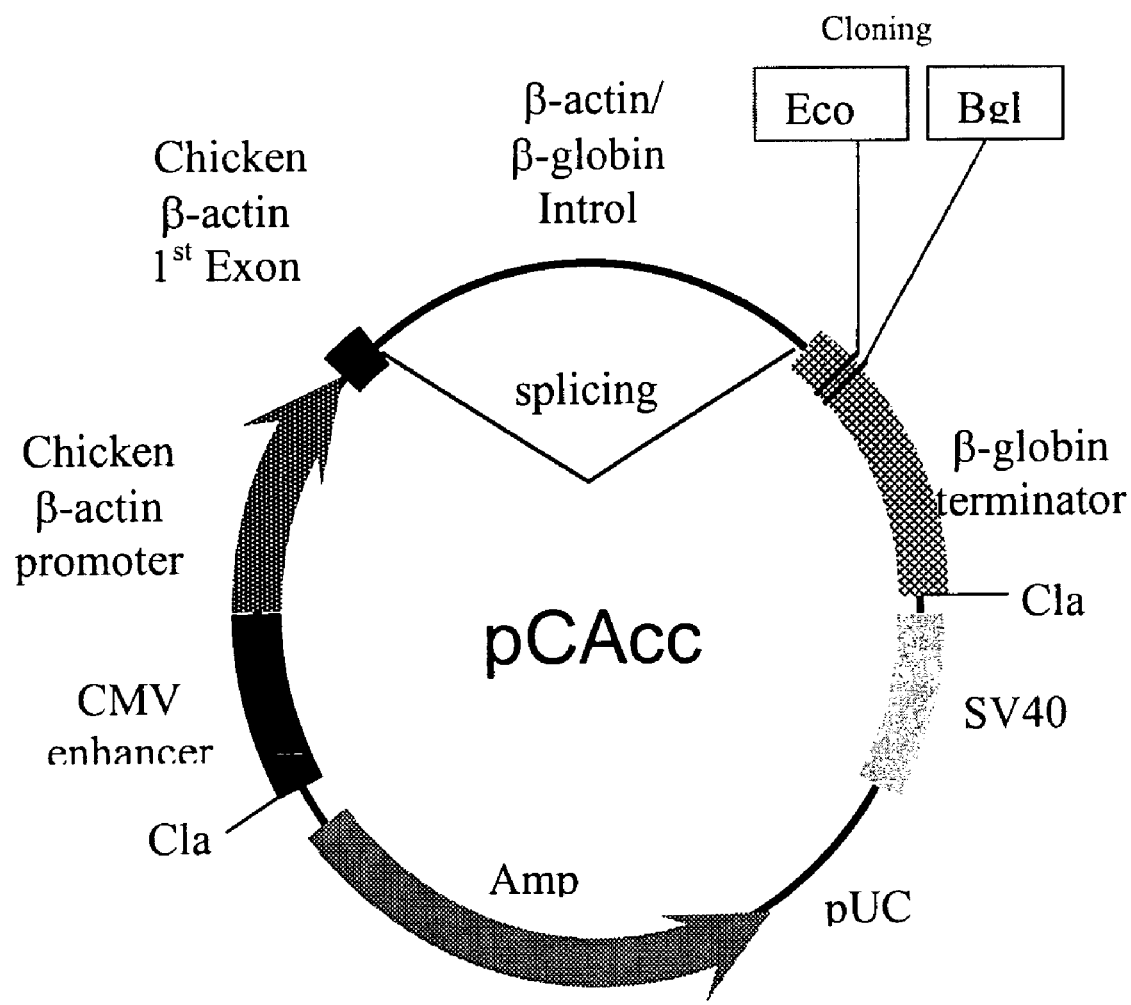
FIG. 6 is a schematic map of the plasmid vector pCAcc.

A chimeric antibody, referred to herein as cSTL4, which comprises the $V_H$ domain of SEQ ID NO: 1 and the $V_L$ domain of SEQ ID NO:2 has been prepared using standard procedures. Briefly, nucleic acid sequences encoding the $V_H$ and $V_L$ domains were amplified by PCR (polymerase chain reaction). The $V_H$ domain was then fused to a human IgG heavy constant region, CH1-H—CH2-CH3, and the $V_L$ domain was fused to a human light constant region, kappa by cloning into the pCAcc plasmid vector.

pCAcc is a potent mammalian cell expression vector driven by CMV-enhancer and b-actin-promotor. This vector is suitable for transient expression. A map of pCAcc is shown in FIG. 6.

Figure 7:
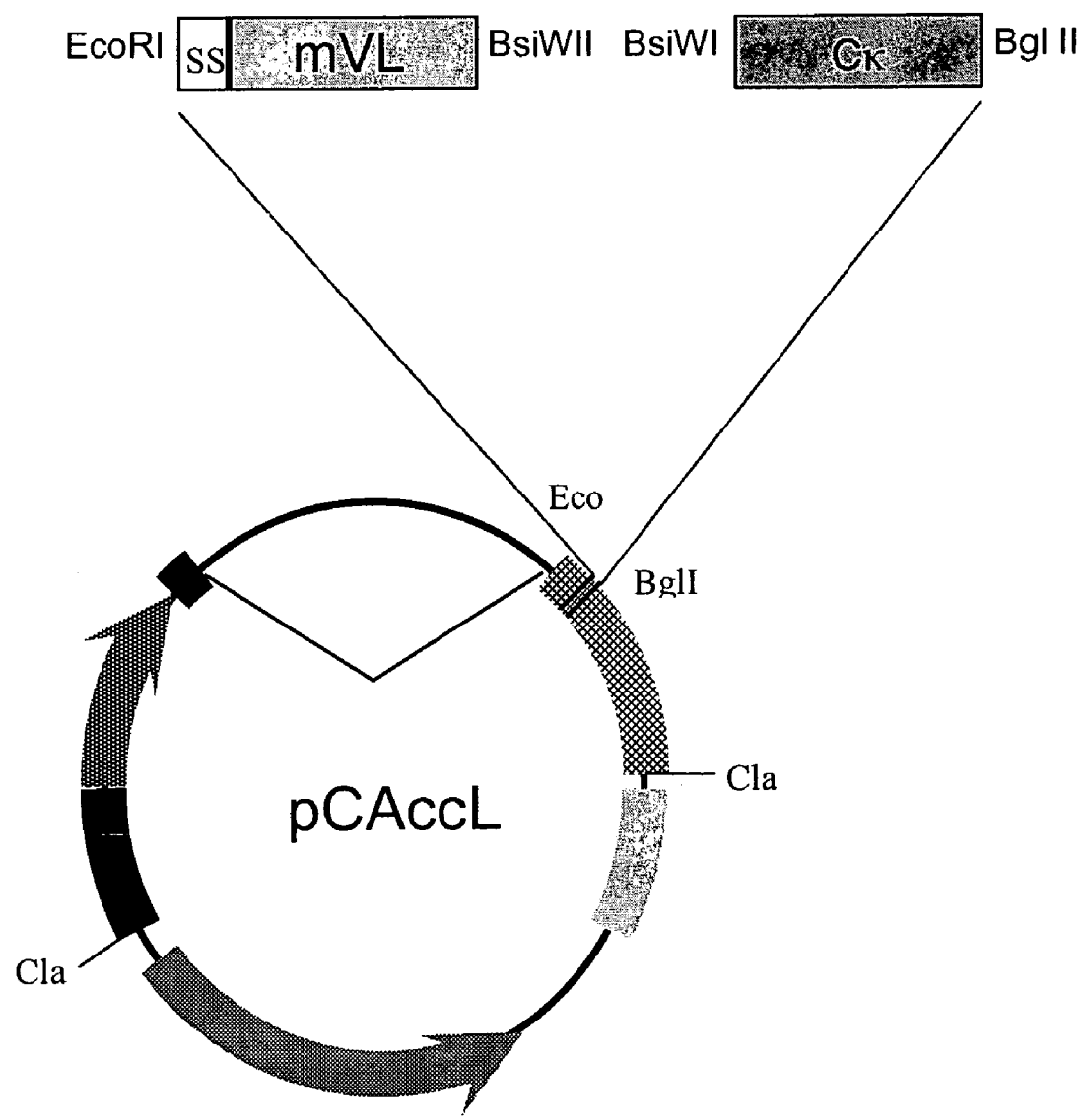
FIG. 7 is a schematic map of the plasmid vector pCAcc with the $V_L$ and Cκ light chain inserted into it (designated herein pCAccL).
Figure 8:
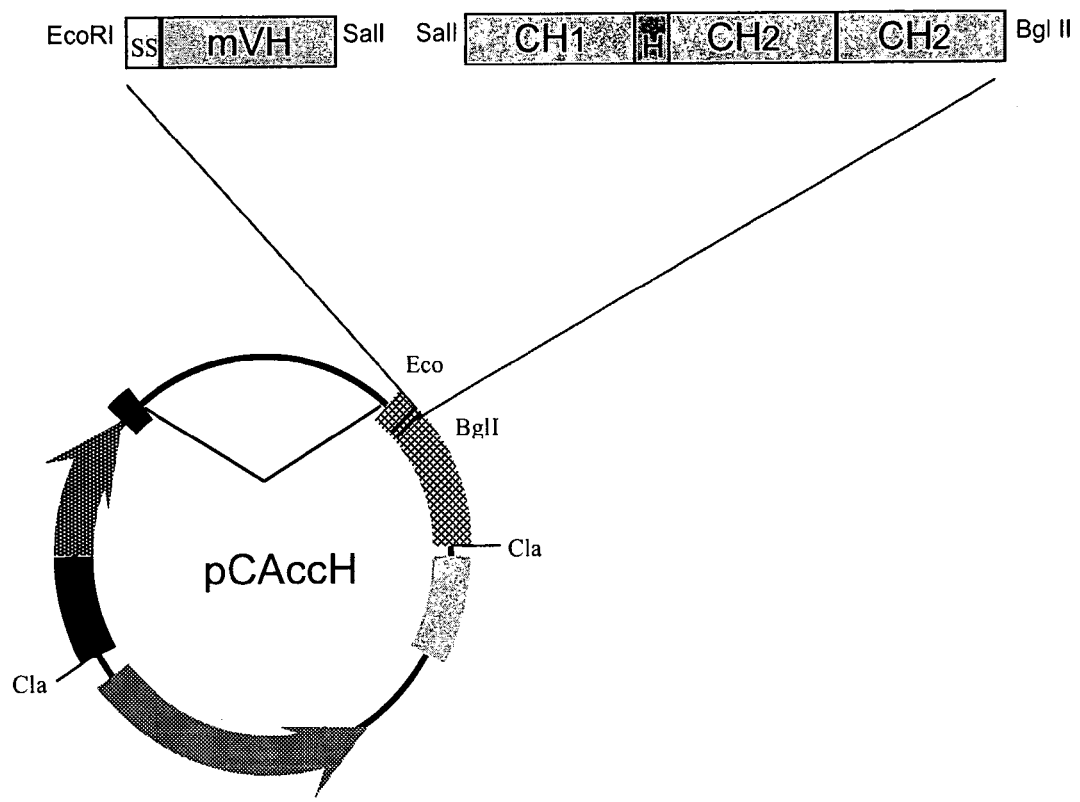
FIG. 8 is a schematic map of the plasmid vector pCAcc with the $V_H$ and CH1-H—CH2-CH2 heavy chain inserted into it (designated herein pCAccH).

FIGS. 7 and 8 show where the light and heavy chains were cloned into the respective pCAcc vectors.

Figure 9:
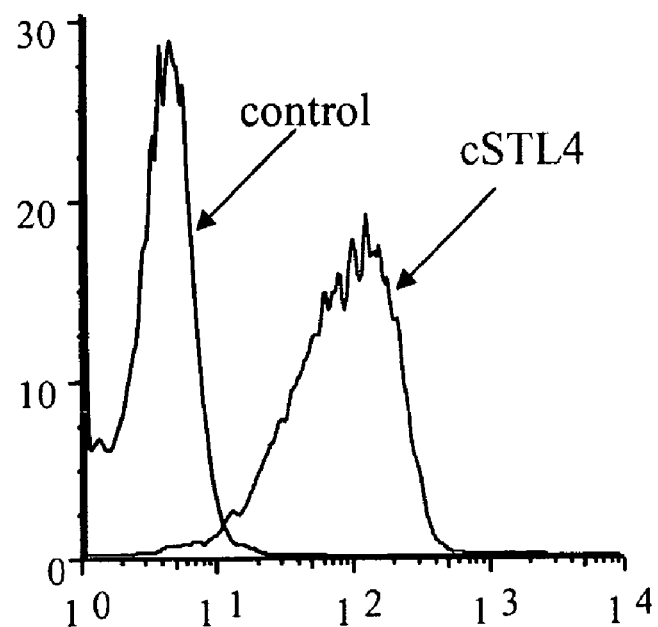
FIG. 9 Shows the characterisation cSTL4 by flow cytometry using Chinese hamster ovary (CHO) cells transfected with human DLL4 (FIG. 9 a) or mock-transfected CHO cells (null control, FIG. 9 b).
Figure 9:
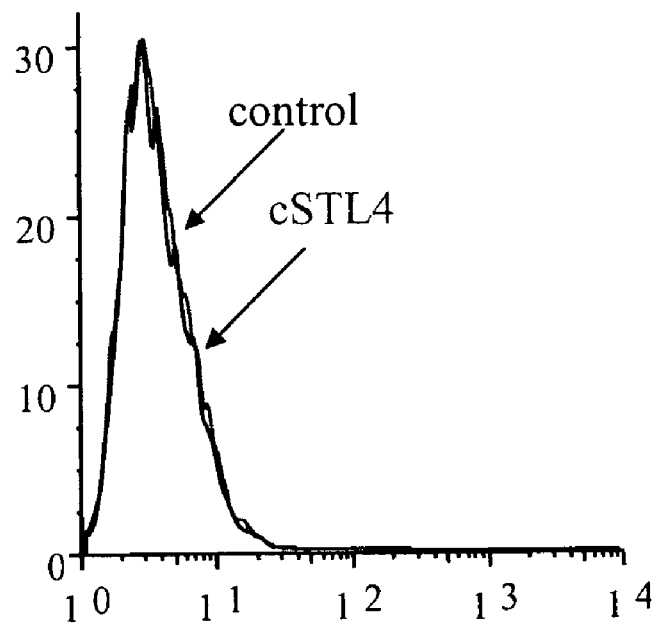

The specific binding of cSTL4 to DLL4 was confirmed using flow cytometry using Chinese hamster ovary (CHO) cells transfected with human DLL4 or non-transfected CHO cells (FIG. 9).

Example 9

Affinity Measurements

Figure 10:
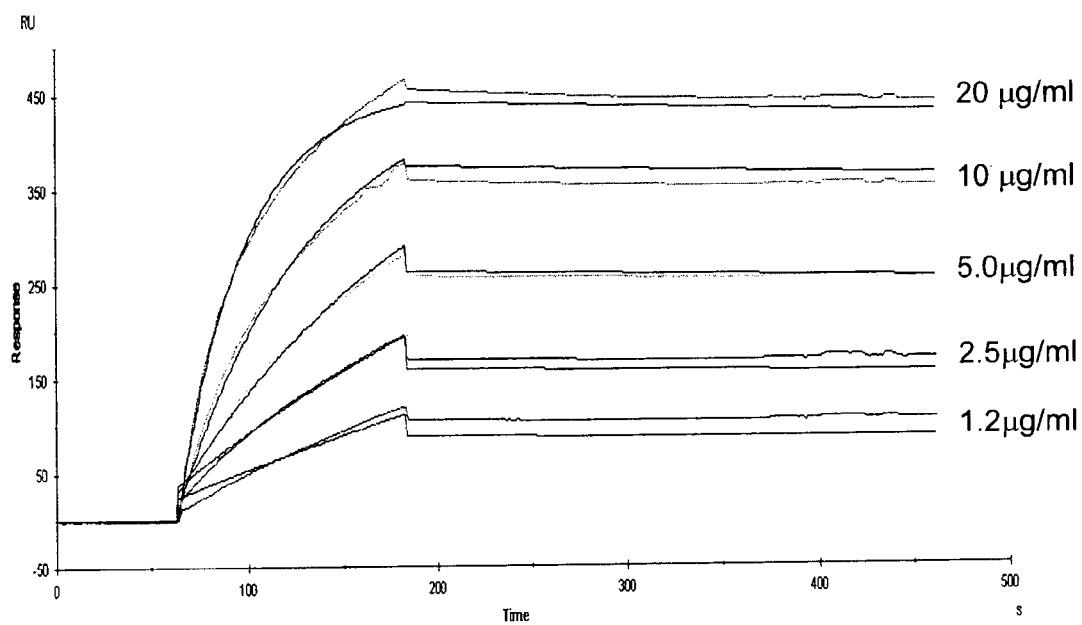
FIG. 10 shows the results of a Biacore assay (Example 9) used to assess the binding affinity of the chimeric anti-Dll4 antibody to immobilized Dll4.

A Biacore A100 analyser was used to assess the binding affinity of the chimeric anti-Dll4 antibody cSTL4. Binding to pure recombinant Dll4 was tested using antibody concentrations of 20, 10, 5, 2.5 and 1.2 µg/ml. The binding curves are shown in FIG. 10. The KD was calculated to be $4.08 \times 10^{-10}$ M. The Ka was $2.45 \times 10^9$ 1/M and the Kd $8.79 \times 10^{-5}$ 1/S.

---

The invention claimed is:

1. An antibody capable of binding to human delta-like ligand 4 (DLL4), which antibody comprises (a) a light chain complementarity determining region (CDR) 1 comprising the amino acid sequence RASSSVSFMH (SEQ ID NO: 6);
 (b) a light chain CDR 2 comprising the amino acid sequence ATSNLTS (SEQ ID NO: 7);
 (c) a light chain CDR3 comprising the amino acid sequence QQWSSNPFT (SEQ ID NO: 8);
 (d) a heavy chain CDR1 comprising the amino acid sequence SYVMH (SEQ ID NO: 3);
 (e) a heavy chain CDR2 comprising the amino acid sequence YIIPYNDGTKYNEKFKG (SEQ ID NO: 4); and
 (f) a heavy chain CDR3 comprising the amino acid sequence SEDYDHFDY (SEQ ID NO: 5).

2. The antibody according to claim 1, wherein said antibody comprises a variable heavy chain domain ($V_H$) domain which has the amino acid sequence of SEQ ID NO: 1, and/or a variable light chain domain ($V_L$) which has the amino acid sequence of SEQ ID NO: 2.

3. The antibody according to claim 1, wherein said antibody comprises one or more of the framework regions disclosed in SEQ ID NOs: 9, 10, 11, 12, 13, 14, 15 or 16.

4. The antibody according to claim 1, wherein said antibody is chimeric or humanised.

5. The antibody according to claim 1, wherein said antibody is a chimeric antibody comprising a human heavy chain constant domain 1 (CH1) and a human kappa light chain constant domain.

6. The antibody according to claim 1, wherein said antibody has a $K_D$ of less than $10\times10^{-10}$ or $5\times10^{-10}$.

7. The antibody according to claim 1, wherein said antibody can inhibit or significantly reduce the function of DLL4 or prevent DLL4 from interacting with one or more of its natural ligands and/or receptors.

8. A nucleic acid molecule comprising a sequence encoding the antibody according to claim 1.

9. A nucleic acid molecule comprising a sequence encoding the antibody according to claim 1, wherein said nucleic acid molecule comprises the nucleic acid molecule as defined in SEQ ID NO: 17 or SEQ ID NO: 18.

10. A recombinant expression vector comprising one or more nucleic acid molecules comprising a sequence encoding the antibody according to claim 1 and a regulatory sequence for the transcription and translation of the protein sequence encoded by said nucleic acid molecule.

11. An isolated host cell comprising a nucleic acid molecule comprising a sequence encoding the antibody according to claim 1 or a recombinant expression vector comprising one or more nucleic acid molecules comprising a sequence encoding the antibody according to claim 1 and a regulatory sequence for the transcription and translation of the protein sequence encoded by said nucleic acid molecule.

12. A method of producing the antibody according to claim 1 comprising a step of culturing an isolated host cell according to claim 11.

13. A fusion protein comprising the antibody according to claim 1 and a further polypeptide sequence.

14. A conjugate comprising the antibody according to claim 1 and a biologically active molecule or medically relevant agent.

15. A method of treatment of a disorder or condition characterised by increased delta-like ligand 4 (DLL4) signalling and/or increased angiogenesis comprising administering to a subject suffering from said disorder or condition or administering to a sample removed from said subject and which is subsequently returned to the subject an effective amount of the antibody according to claim 1; a fusion protein comprising the antibody according to claim 1 and a further polypeptide sequence; or a conjugate comprising the antibody according to claim 1 and a biologically active molecule or medically relevant agent.

16. The method according to claim 15, wherein said disorder or condition is selected from atherosclerosis, arthritis, ocular neovascularisation, endometriosis, uterine fibroids, pre-eclampsia and cancer.

17. The method according to claim 16, wherein said disorder or condition is selected from prostate cancer and pancreatic cancer.

18. A composition comprising the antibody according to claim 1; a fusion protein comprising the antibody according to claim 1 and a further polypeptide sequence; a conjugate comprising the antibody according to claim 1 and a biologically active molecule or medically relevant agent; a nucleic acid molecule comprising a sequence encoding the antibody according to claim 1; or a vector comprising a sequence encoding the antibody according to claim 1, and a pharmaceutically acceptable excipient, carrier, diluent, buffer or stabilizer.

* * * * *

SEQUENCE LISTING

```
<160> NUMBER OF SEQ ID NOS: 22

<210> SEQ ID NO 1
<211> LENGTH: 121
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(118)
<223> OTHER INFORMATION: variable heavy chain

<400> SEQUENCE: 1

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
```

```
                     20                  25                  30
Val Met His Trp Val Lys Gln Lys Pro Gly Gln Gly Leu Glu Trp Ile
        35                  40                  45

Gly Tyr Ile Ile Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Ser Glu Asp Tyr Asp His Phe Asp Tyr Trp Gly Gln Gly Thr
            100                 105                 110

Thr Val Thr Val Ser Ser Ala Lys Thr
        115                 120

<210> SEQ ID NO 2
<211> LENGTH: 109
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(106)
<223> OTHER INFORMATION: variable light chain

<400> SEQUENCE: 2

Gln Ile Val Leu Ser Gln Ser Pro Val Ile Leu Ser Ala Ser Pro Gly
1               5                   10                  15

Glu Lys Val Thr Met Thr Cys Arg Ala Ser Ser Ser Val Ser Phe Met
                20                  25                  30

His Trp Tyr Gln Gln Lys Pro Gly Ser Ser Pro Lys Pro Trp Ile Tyr
            35                  40                  45

Ala Thr Ser Asn Leu Thr Ser Gly Val Pro Thr Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Lys Arg Ala Asp
            100                 105

<210> SEQ ID NO 3
<211> LENGTH: 5
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(5)
<223> OTHER INFORMATION: heavy chain CDR 1

<400> SEQUENCE: 3

Ser Tyr Val Met His
1               5

<210> SEQ ID NO 4
<211> LENGTH: 17
<212> TYPE: PRT
<213> ORGANISM: artificial sequence
<220> FEATURE:
<223> OTHER INFORMATION: partial antibody
<220> FEATURE:
```

```
<221> NAME/KEY: PEPTIDE
<222> LOCATION: (1)..(17)
<223> OTHER INFORMATION: heavy chain CDR 2

<400> SEQUENCE: 4

Tyr Ile Ile Pro Tyr Asn Asp Gly Thr Lys Tyr Asn Glu Lys Phe Lys
1               5                   10                  15
Gly

<210> SEQ ID NO 5
<211> LENGTH: 9
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(9)
<223> OTHER INFORMATION: heavy chain CDR 3

<400> SEQUENCE: 5

Ser Glu Asp Tyr Asp His Phe Asp Tyr
1               5

<210> SEQ ID NO 6
<211> LENGTH: 10
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(10)
<223> OTHER INFORMATION: light chain CDR 1

<400> SEQUENCE: 6

Arg Ala Ser Ser Ser Val Ser Phe Met His
1               5                   10

<210> SEQ ID NO 7
<211> LENGTH: 7
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(7)
<223> OTHER INFORMATION: light chain CDR2

<400> SEQUENCE: 7

Ala Thr Ser Asn Leu Thr Ser
1               5

<210> SEQ ID NO 8
<211> LENGTH: 9
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(9)
<223> OTHER INFORMATION: light chain CDR3

<400> SEQUENCE: 8

Gln Gln Trp Ser Ser Asn Pro Phe Thr
1               5
```

```
<210> SEQ ID NO 9
<211> LENGTH: 30
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(30)
<223> OTHER INFORMATION: heavy framework 1

<400> SEQUENCE: 9

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr
            20                  25                  30

<210> SEQ ID NO 10
<211> LENGTH: 14
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(14)
<223> OTHER INFORMATION: heavy framework 2

<400> SEQUENCE: 10

Trp Val Lys Gln Lys Pro Gly Gln Gly Leu Glu Trp Ile Gly
1               5                   10

<210> SEQ ID NO 11
<211> LENGTH: 32
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(32)
<223> OTHER INFORMATION: heavy framework 3

<400> SEQUENCE: 11

Lys Ala Thr Leu Thr Ser Asp Lys Ser Ser Thr Ala Tyr Met Glu
1               5                   10                  15

Leu Ser Ser Leu Thr Ser Glu Asp Ser Ala Val Tyr Tyr Cys Ala Arg
            20                  25                  30

<210> SEQ ID NO 12
<211> LENGTH: 14
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(11)
<223> OTHER INFORMATION: heavy framework 4

<400> SEQUENCE: 12

Trp Gly Gln Gly Thr Thr Val Thr Val Ser Ser Ala Lys Thr
1               5                   10

<210> SEQ ID NO 13
<211> LENGTH: 23
<212> TYPE: PRT
<213> ORGANISM: artificial sequence
<220> FEATURE:
<223> OTHER INFORMATION: partial antibody
```

```
<220> FEATURE:
<221> NAME/KEY: PEPTIDE
<222> LOCATION: (1)..(23)
<223> OTHER INFORMATION: light framework 1

<400> SEQUENCE: 13

Gln Ile Val Leu Ser Gln Ser Pro Val Ile Leu Ser Ala Ser Pro Gly
1               5                   10                  15

Glu Lys Val Thr Met Thr Cys
            20

<210> SEQ ID NO 14
<211> LENGTH: 15
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(15)
<223> OTHER INFORMATION: light framework 2

<400> SEQUENCE: 14

Trp Tyr Gln Gln Lys Pro Gly Ser Ser Pro Lys Pro Trp Ile Tyr
1               5                   10                  15

<210> SEQ ID NO 15
<211> LENGTH: 32
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(32)
<223> OTHER INFORMATION: light framework 3

<400> SEQUENCE: 15

Gly Val Pro Thr Arg Phe Ser Gly Ser Gly Ser Gly Thr Ser Tyr Ser
1               5                   10                  15

Leu Thr Ile Ser Arg Val Glu Ala Glu Asp Ala Ala Thr Tyr Tyr Cys
            20                  25                  30

<210> SEQ ID NO 16
<211> LENGTH: 13
<212> TYPE: PRT
<213> ORGANISM: artificial sequence
<220> FEATURE:
<223> OTHER INFORMATION: partial antibody
<220> FEATURE:
<221> NAME/KEY: PEPTIDE
<222> LOCATION: (1)..(11)
<223> OTHER INFORMATION: light framework 4

<400> SEQUENCE: 16

Phe Gly Ser Gly Thr Lys Leu Glu Ile Lys Arg Ala Asp
1               5                   10

<210> SEQ ID NO 17
<211> LENGTH: 478
<212> TYPE: DNA
<213> ORGANISM: artificial sequence
<220> FEATURE:
<223> OTHER INFORMATION: nucleotide sequence encoding variable heavy
      chain
<220> FEATURE:
<221> NAME/KEY: misc_feature
<222> LOCATION: (1)..(478)
<223> OTHER INFORMATION: cDNA sequence
```

<400> SEQUENCE: 17

```
atggaatgga gttggatatt tctctttctc ctgtcaggaa ctgcaggtgt ccactctgag    60
gtccagctgc agcagtctgg acctgagctg gtaaagcctg ggcttcagt gaagatgtcc    120
tgcaaggctt ctggatacac attcactagt tatgttatgc actgggtgaa gcagaagcct    180
gggcagggcc ttgagtggat tggatatatt attccttaca tgatggtac aagtacaat    240
gagaagttca aggcaaggc cacactgact tcagacaaat cctccagcac agcctacatg    300
gagctcagca gcctgaccte tgaggactct gcggtctatt actgtgctag atcagaggat    360
tacgaccact ttgactactg gggccaaggc accactctca cagtctcctc agccaaaacg    420
acacccccat ctgtctatcc actggcccct ggatctgctg cccaaactaa ctccatgg    478
```

<210> SEQ ID NO 18
<211> LENGTH: 395
<212> TYPE: DNA
<213> ORGANISM: artificial sequence
<220> FEATURE:
<223> OTHER INFORMATION: nucleotide sequence encoding variable light
      chain
<220> FEATURE:
<221> NAME/KEY: misc_feature
<222> LOCATION: (1)..(395)
<223> OTHER INFORMATION: cDNA

<400> SEQUENCE: 18

```
atggattttc aagtgcagat tttcagcttc ctgctaatca gtgcttcagt cataatgtcc    60
agaggacaaa ttgttctctc ccagtctcca gtaatcctgt ctgcatctcc aggggagaag    120
gtcacaatga cttgcagggc cagctcaagt gtaagtttca tgcactggta ccagcagaag    180
ccaggatcct cccccaaacc ctggatttat gccacatcca acctgacttc tggagtccct    240
actcgcttca gtggcagtgg gtctgggacc tcttactctc tcacaatcag cagagtggag    300
gctgaagatg ctgccactta ttactgccag cagtggagta gtaacccatt cacgttcggc    360
tcggggacaa agttggaaat aaaacgggct gatgc    395
```

<210> SEQ ID NO 19
<211> LENGTH: 3426
<212> TYPE: DNA
<213> ORGANISM: Mus musculus

<400> SEQUENCE: 19

```
ctcgcaggct aggaacccga ggccaagagc tgcagccaaa gtcacttggg tgcagtgtac    60
tccctcacta gcccgctcga gaccctagga tttgctccag acacgtact tagagcagcc    120
accgcccagt cgccctcacc tggattacct accgaggcat cgagcagcgg agttttgag    180
aaggcgacaa gggagcagcg tcccgagggg aatcagcttt tcaggaactc ggctggcaga    240
cgggacttgc gggagagcga catccctaac aagcagattc ggagtccgg agtggagagg    300
acaccccaag ggatgacgcc tgcgtcccgg agcgcctgtc gctgggcgct actgctgctg    360
gcggtactgt ggccgcagca gcgcgctgcg ggctccggca tcttccagct gcggctgcag    420
gagttcgtca accagcgcgg tatgctggcc aatgggcagt cctgcgaacc gggctgccgg    480
acttttcttcc gcatttgcct taagcacttc aggcaacct tctccgaggg accctgcacc    540
tttggcaatg tctccacgcc ggtattgggc accaactcct cgtcgtcag ggacaagaat    600
agcggcagtg tcgcaacccc tctgcagttg cccttcaatt tcaccggcc gggaaccttc    660
tcactcaaca tccaagcttg gcacacaccg ggagacgacc tgcggccaga gacttcgcca    720
ggaaactctc tcatcagcca aatcatcatc caaggctctc ttgctgtggg taagatttgg    780
```

```
cgaacagacg agcaaaatga caccctcacc agactgagct actcttaccg ggtcatctgc    840
agtgacaact actatggaga gagctgttct cgcctatgca agaagcgcga tgaccacttc    900
ggacattatg agtgccagcc agatggcagc ctgtcctgcc tgccgggctg gactgggaag    960
tactgtgacc agcctatatg tctttctggc tgtcatgagc agaatggtta ctgcagcaag   1020
ccagatgagt gcatctgccg tccaggttgg cagggtcgcc tgtgcaatga atgtatcccc   1080
cacaatggct gtcgtcatgg cacctgcagc atccctggc agtgtgcctg cgatgaggga   1140
tggggaggtc tgttttgtga ccaagatctc aactactgta ctcaccactc tccgtgcaag   1200
aatggatcaa cgtgttccaa cagtgggcca aagggttata cctgcacctg tctcccaggc   1260
tacactggtg agcactgtga gctgggactc agcaagtgtg ccagcaaccc ctgtcgaaat   1320
ggtggcagct gtaaggacca ggagaatagc taccactgcc tgtgtccccc aggctactat   1380
ggccagcact gtgagcatag taccttgacc tgtgcggact cacctgcctt caatgggggc   1440
tcttgccggg agcgcaacca ggggtccagt tatgcctgcg aatgccccc caactttacc   1500 ggctctaact gtgagaagaa agtagacagg tgtaccagca acccgtgtgc caatggaggc   1560
cagtgcctga acagaggtcc aagccgaacc tgccgctgcc ggcctggatt cacaggcacc   1620
cactgtgaac tgcacatcag cgattgtgcc cgaagtccct gtgcccacgg gggcacttgc   1680
cacgatctgg agaatgggcc tgtgtgcacc tgccccgctg gcttctctgg caggcgctgc   1740
gaggtgcgga taacccacga tgcctgtgcc tccggaccct gcttcaatgg gccacctgc   1800 tacactggcc tctccccaaa caacttcgtc tgcaactgtc cttatggctt tgtgggcagc   1860
cgctgcgagt ttcccgtggg cttgccaccc agcttcccct gggtagctgt ctcgctgggc   1920
gtggggctag tggtactgct ggtgctgctg gtcatggtgg tagtggctgt gcggcagctg   1980
cggcttcgga ggcccgatga cgagagcagg gaagccatga caatctgtc agacttccag   2040 aaggacaacc taatccctgc cgcccagctc aaaaacacaa accagaagaa ggagctggaa   2100
gtggactgtg gtctggacaa gtccaattgt ggcaaactgc agaaccacac attggactac   2160
aatctagccc cgggactcct aggacggggc agcatgcctg gaagtatcc tcacagtgac   2220 aagagcttag gagagaaggt gccacttcgg ttacacagtg agaagccaga gtgtcgaata   2280
tcagccattt gctctcccag ggactctatg taccaatcag tgtgtttgat atcagaagag   2340
aggaacgagt gtgtgattgc cacagaggta aaggcagga gcctactcag acacccagct   2400
ccggcccagc agctgggcct tccttctgca ttgtttacat tgcatcctgt atgggacatc   2460
tttagtatgc acagtgctgc tctgcggagg aggagggaat ggcatgaact gaacagactg   2520
tgaacccgcc aagagttgca ccggctctgc acacctccag gagtctgcct ggcttcagat   2580
gggcagcccc gccaagggaa cagagttgag gagttagagg agcatcagtt gagctgatat   2640
ctaaggtgcc tctcgaactt ggacttgctc tgccaacagt ggtcatcatg gagctcttga   2700
ctgttctcca gagagtggca gtggccctag tgggtcttgg cgctgctgta gctcctgtgg   2760
gcatctgtat ttccaaagtg cctttgccca gactccatcc tcacagctgg gcccaaatga   2820
gaaagcagag aggaggcttg caaaggatag gcctcccgca ggcagaacag ccttggagtt   2880
tggcattaag caggagctac tctgcaggtg aggaaagccc gaggagggga cacgtgtgac   2940
tcctgcctcc aacccagca gtggggtgc cacctgcagc ctctaggcaa gagttggtcc   3000
ttcccctggt cctggtgcct ctgggctcat gtgaacagat gggcttaggg cacgcccctt   3060
ttgccagcca ggggtacagg cctcactggg gagctcaggg ccttcatgct aaactcccaa   3120
taagggagat gggggggaagg gggctgtggc ctaggcccctt ccctccctca cacccatttt   3180
```

-continued

```
tgggcccttg agcctgggct ccaccagtgc ccactgttgc cccgagacca accttgaagc    3240
cgattttcaa aaatcaataa tatgaggttt tgttttgtag tttattttgg aatctagtat    3300
tttgataatt taagaatcag aagcactggc ctttctacat tttataacat tattttgtat    3360
ataatgtgta tttataatat gaaacagatg tgtacataaa aaaaaaaaaa aaaaaaaaaa    3420
aaaaaa                                                              3426
```

```
<210> SEQ ID NO 20
<211> LENGTH: 684
<212> TYPE: PRT
<213> ORGANISM: Mus musculus

<400> SEQUENCE: 20
```

| | | | | | | | | | | | | | | | |
|---|---|---|---|---|---|---|---|---|---|---|---|---|---|---|---|
| Met | Thr | Pro | Ala | Ser | Arg | Ser | Ala | Cys | Arg | Trp | Ala | Leu | Leu | Leu | Leu |
| 1 | | | | 5 | | | | | 10 | | | | | 15 | |
| Ala | Val | Leu | Trp | Pro | Gln | Gln | Arg | Ala | Ala | Gly | Ser | Gly | Ile | Phe | Gln |
| | | | 20 | | | | | 25 | | | | | 30 | | |
| Leu | Arg | Leu | Gln | Glu | Phe | Val | Asn | Gln | Arg | Gly | Met | Leu | Ala | Asn | Gly |
| | | 35 | | | | | 40 | | | | | 45 | | | |
| Gln | Ser | Cys | Glu | Pro | Gly | Cys | Arg | Thr | Phe | Phe | Arg | Ile | Cys | Leu | Lys |
| | 50 | | | | | 55 | | | | | 60 | | | | |
| His | Phe | Gln | Ala | Thr | Phe | Ser | Glu | Gly | Pro | Cys | Thr | Phe | Gly | Asn | Val |
| 65 | | | | | 70 | | | | | 75 | | | | | 80 |
| Ser | Thr | Pro | Val | Leu | Gly | Thr | Asn | Ser | Phe | Val | Val | Arg | Asp | Lys | Asn |
| | | | | 85 | | | | | 90 | | | | | 95 | |
| Ser | Gly | Ser | Gly | Arg | Asn | Pro | Leu | Gln | Leu | Pro | Phe | Asn | Phe | Thr | Trp |
| | | | 100 | | | | | 105 | | | | | 110 | | |
| Pro | Gly | Thr | Phe | Ser | Leu | Asn | Ile | Gln | Ala | Trp | His | Thr | Pro | Gly | Asp |
| | | | | 115 | | | | | 120 | | | | | 125 | |
| Asp | Leu | Arg | Pro | Glu | Thr | Ser | Pro | Gly | Asn | Ser | Leu | Ile | Ser | Gln | Ile |
| | 130 | | | | | 135 | | | | | 140 | | | | |
| Ile | Ile | Gln | Gly | Ser | Leu | Ala | Val | Gly | Lys | Ile | Trp | Arg | Thr | Asp | Glu |
| 145 | | | | | 150 | | | | | 155 | | | | | 160 |
| Gln | Asn | Asp | Thr | Leu | Thr | Arg | Leu | Ser | Tyr | Ser | Tyr | Arg | Val | Ile | Cys |
| | | | | 165 | | | | | 170 | | | | | 175 | |
| Ser | Asp | Asn | Tyr | Tyr | Gly | Glu | Ser | Cys | Ser | Arg | Leu | Cys | Lys | Lys | Arg |
| | | | 180 | | | | | 185 | | | | | 190 | | |
| Asp | Asp | His | Phe | Gly | His | Tyr | Glu | Cys | Gln | Pro | Asp | Gly | Ser | Leu | Ser |
| | | 195 | | | | | 200 | | | | | 205 | | | |
| Cys | Leu | Pro | Gly | Trp | Thr | Gly | Lys | Tyr | Cys | Asp | Gln | Pro | Ile | Cys | Leu |
| | 210 | | | | | 215 | | | | | 220 | | | | |
| Ser | Gly | Cys | His | Glu | Gln | Asn | Gly | Tyr | Cys | Ser | Lys | Pro | Asp | Glu | Cys |
| 225 | | | | | 230 | | | | | 235 | | | | | 240 |
| Ile | Cys | Arg | Pro | Gly | Trp | Gln | Gly | Arg | Leu | Cys | Asn | Glu | Cys | Ile | Pro |
| | | | | 245 | | | | | 250 | | | | | 255 | |
| His | Asn | Gly | Cys | Arg | His | Gly | Thr | Cys | Ser | Ile | Pro | Trp | Gln | Cys | Ala |
| | | | 260 | | | | | 265 | | | | | 270 | | |
| Cys | Asp | Glu | Gly | Trp | Gly | Gly | Leu | Phe | Cys | Asp | Gln | Asp | Leu | Asn | Tyr |
| | | 275 | | | | | 280 | | | | | 285 | | | |
| Cys | Thr | His | His | Ser | Pro | Cys | Lys | Asn | Gly | Ser | Thr | Cys | Ser | Asn | Ser |
| | 290 | | | | | 295 | | | | | 300 | | | | |
| Gly | Pro | Lys | Gly | Tyr | Thr | Cys | Thr | Cys | Leu | Pro | Gly | Tyr | Thr | Gly | Glu |
| 305 | | | | | 310 | | | | | 315 | | | | | 320 |
| His | Cys | Glu | Leu | Gly | Leu | Ser | Lys | Cys | Ala | Ser | Asn | Pro | Cys | Arg | Asn |

```
                    325                 330                 335
Gly Gly Ser Cys Lys Asp Gln Glu Asn Ser Tyr His Cys Leu Cys Pro
                340                 345                 350
Pro Gly Tyr Tyr Gly Gln His Cys Glu His Ser Thr Leu Thr Cys Ala
            355                 360                 365
Asp Ser Pro Cys Phe Asn Gly Gly Ser Cys Arg Glu Arg Asn Gln Gly
        370                 375                 380
Ser Ser Tyr Ala Cys Glu Cys Pro Pro Asn Phe Thr Gly Ser Asn Cys
385                 390                 395                 400
Glu Lys Lys Val Asp Arg Cys Thr Ser Asn Pro Cys Ala Asn Gly Gly
                405                 410                 415
Gln Cys Leu Asn Arg Gly Pro Ser Arg Thr Cys Arg Cys Arg Pro Gly
                420                 425                 430
Phe Thr Gly Thr His Cys Glu Leu His Ile Ser Asp Cys Ala Arg Ser
            435                 440                 445
Pro Cys Ala His Gly Gly Thr Cys His Asp Leu Glu Asn Gly Pro Val
        450                 455                 460
Cys Thr Cys Pro Ala Gly Phe Ser Gly Arg Arg Cys Glu Val Arg Ile
465                 470                 475                 480
Thr His Asp Ala Cys Ala Ser Gly Pro Cys Phe Asn Gly Ala Thr Cys
                485                 490                 495
Tyr Thr Gly Leu Ser Pro Asn Asn Phe Val Cys Pro Tyr Gly Phe
                500                 505                 510
Val Gly Ser Arg Cys Glu Phe Pro Val Gly Leu Pro Pro Ser Phe Pro
            515                 520                 525
Trp Val Ala Val Ser Leu Gly Val Gly Leu Val Val Leu Leu Val Leu
        530                 535                 540
Leu Val Met Val Val Ala Val Arg Gln Leu Arg Leu Arg Arg Pro
545                 550                 555                 560
Asp Asp Glu Ser Glu Ala Met Asn Asn Leu Ser Asp Phe Gln Lys Asp
                565                 570                 575
Asn Leu Ile Pro Ala Ala Gln Leu Lys Asn Thr Asn Gln Lys Lys Glu
            580                 585                 590
Leu Glu Val Asp Cys Gly Leu Asp Lys Ser Asn Cys Gly Lys Leu Gln
        595                 600                 605
Asn His Thr Leu Asp Tyr Asn Leu Ala Pro Gly Leu Leu Gly Arg Gly
        610                 615                 620
Ser Met Pro Gly Lys Tyr Pro His Ser Asp Lys Ser Leu Gly Glu Lys
625                 630                 635                 640
Val Pro Leu Arg Leu His Ser Glu Lys Pro Glu Cys Arg Ile Ser Ala
                645                 650                 655
Ile Cys Ser Pro Arg Asp Ser Met Tyr Gln Ser Val Cys Leu Ile Ser
            660                 665                 670
Glu Glu Arg Asn Glu Cys Val Ile Ala Thr Glu Val
                675                 680

<210> SEQ ID NO 21
<211> LENGTH: 3383
<212> TYPE: DNA
<213> ORGANISM: Homo sapiens

<400> SEQUENCE: 21
gctgcgcgca ggccgggaac acgaggccaa gagccgcagc cccagccgcc ttggtgcagc    60
gtacaccggc actagcccgc ttgcagcccc aggattagac agaagacgcg tcctcggcgc   120
```

```
ggtcgccgcc cagccgtagt cacctggatt acctacagcg gcagctgcag cggagccagc    180
gagaaggcca aggggagca gcgtcccgag aggagcgcct cttttcaggg accccgccgg    240
ctggcggacg cgcgggaaag cggcgtcgcg aacagagcca gattgagggc ccgcgggtgg    300
agagagcgac gcccgagggg atggcggcag cgtcccggag cgcctctggc tgggcgctac    360
tgctgctggt ggcactttgg cagcagcgcg cggccggctc cggcgtcttc cagctgcagc    420
tgcaggagtt catcaacgag cgcggcgtac tggccagtgg gcggccttgc gagcccggct    480
gccggacttt cttccgcgtc tgccttaagc acttccaggc ggtcgtctcg cccggaccct    540
gcaccttcgg gaccgtctcc acgccggtat tgggcaccaa ctccttcgct gtccgggacg    600
acagtagcgg cggggggcgc aaccctctcc aactgcccct caatttcacc tggccgggta    660
ccttctcgct catcatcgaa gcttggcacg cgccaggaga cgacctgcgg ccagaggcct    720
tgccaccaga tgcactcatc agcaagatcg ccatccaggg ctccctagct gtgggtcaga    780
actggttatt ggatgagcaa accagcaccc tcacaaggct gcgctactct taccgggtca    840
tctgcagtga caactactat ggagacaact gctcccgcct gtgcaagaag cgcaatgacc    900
acttcggcca ctatgtgtgc cagccagatg caacttgtc ctgcctgccc ggttggactg    960
gggaatattg ccaacagcct atctgtcttt cgggctgtca tgaacagaat ggctactgca   1020
gcaagccagc agagtgcctc tgccgcccag gctggcaggg ccggctgtgt aacgaatgca   1080
tcccccacaa tggctgtcgc cacggcacct gcagcactcc ctggcaatgt acttgtgatg   1140
agggctgggg aggcctgttt tgtgaccaag atctcaacta ctgcacccac cactccccat   1200
gcaagaatgg ggcaacgtgc tccaacagtg ggcagcgaag ctacacctgc acctgtcgcc   1260
caggctacac tggtgtggac tgtgagctgg agctcagcga gtgtgacagc aaccctgtc   1320
gcaatggagg cagctgtaag gaccaggagg atggctacca ctgcctgtgt cctccgggct   1380
actatggcct gcattgtgaa cacagcacct tgagctgcgc cgactccccc tgcttcaatg   1440
ggggctcctg ccgggagcgc aaccagggg ccaactatgc ttgtgaatgt cccccccaact   1500
tcaccggctc caactgcgag aagaaagtgg acaggtgcac cagcaacccc tgtgccaacg   1560
ggggacagtg cctgaaccga ggtccaagcc gcatgtgccg ctgccgtcct ggattcacgg   1620
gcacctactg tgaactccac gtcagcgact gtgcccgtaa cccttgcgcc acggtggca   1680
cttgccatga cctggagaat gggctcatgt gcacctgccc tgccggcttc tctggccgac   1740
gctgtgaggt gcggacatcc atcgatgcct gtgcctcgag tccctgcttc aacagggcca   1800
cctgctacac cgacctctcc acagacacct ttgtgtgcaa ctgcccttat ggctttgtgg   1860
gcagccgctg cgagttcccc gtgggcttgc cgcccagctt ccccctgggtg gccgtctcgc   1920
tgggtgtggg gctggcagtg ctgctggtac tgctgggcat ggtggcagtg gctgtgcggc   1980
agctgcggct tcgacggccg gacgacggca gcagggaagc catgaacaac ttgtcggact   2040
tccagaagga caacctgatt cctgccgccc agcttaaaaa cacaaaccag aagaaggagc   2100
tggaagtgga ctgtggcctg gacaagtcca actgtggcaa acagcaaaac cacacattgg   2160
actataatct gccccagggg cccctgggg ggggaccat gccaggaaag tttccccaca   2220
gtgacaagag cttaggagag aaggcgccac tgcggttaca cagtgaaaag ccagagtgtc   2280
ggatatcagc gatatgctcc cccagggact ccatgtacca gtctgtgtgt ttgatatcag   2340
aggagaggaa tgaatgtgtc attgccacgg aggtataagg caggagccta cctggacatc   2400
cctgctcagc cccgcggctg gaccttcctt ctgcattgtt tacattgcat cctggatggg   2460
acgttttttca tatgcaacgt gctgctctca ggaggaggag ggaatggcag gaaccggaca   2520
```

| | |
|---|---|
| gactgtgaac ttgccaagag atgcaatacc cttccacacc tttgggtgtc tgtctggcat | 2580 |
| cagattggca gctgcaccaa ccagaggaac agaagagaag agagatgcca ctgggcactg | 2640 |
| ccctgccagt agtggccttc agggggctcc ttccggggct ccggcctgtt ttccagagag | 2700 |
| agtggcagta gccccatggg gcccggagct gctgtggcct ccactggcat ccgtgtttcc | 2760 |
| aaaagtgcct ttggcccagg ctccacggcg acagttgggc ccaaatcaga aggagagag | 2820 |
| ggggccaatg agggcagggc ctcctgtggg ctggaaaacc actgggtgcg tctcttgctg | 2880 |
| gggtttgccc tggaggtgag gtgagtgctc gagggagggg agtgctttct gccccatgcc | 2940 |
| tccaactact gtatgcaggc ctggctctct ggtctaggcc cttgggcaa gaatgtccgt | 3000 |
| ctacccggct ccaccaccc tctggccctg gcttctgta agcagacagg cagagggcct | 3060 |
| gcccctccca ccagccaagg gtgccaggcc taactgggc actcagggca gtgtgttgga | 3120 |
| aattccactg aggggaaat caggtgctgc ggccgcctgg gccctttcct ccctcaagcc | 3180 |
| catctccaca acctcgagcc tgggctctgg tccactactg ccccagacca ccctcaaagc | 3240 |
| tggtcttcag aaatcaataa tatgagtttt tattttgttt tttttttttt ttttgtagtt | 3300 |
| tattttggag tctagtattt caataattta agaatcagaa gcactgacct ttctacattt | 3360 |
| tataacatta ttttgtatat aat | 3383 |

<210> SEQ ID NO 22
<211> LENGTH: 682
<212> TYPE: PRT
<213> ORGANISM: Homo sapiens

<400> SEQUENCE: 22

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

-continued

```
Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
            245                 250                 255

Asn Gly Cys Arg His Gly Thr Cys Ser Thr Pro Trp Gln Cys Thr Cys
        260                 265                 270

Asp Glu Gly Trp Gly Gly Leu Phe Cys Asp Gln Asp Leu Asn Tyr Cys
    275                 280                 285

Thr His His Ser Pro Cys Lys Asn Gly Ala Thr Cys Ser Asn Ser Gly
290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
            325                 330                 335

Gly Ser Cys Lys Asp Gln Glu Asp Gly Tyr His Cys Leu Cys Pro Pro
        340                 345                 350

Gly Tyr Tyr Gly Leu His Cys Glu His Ser Thr Leu Ser Cys Ala Asp
    355                 360                 365

Ser Pro Cys Phe Asn Gly Gly Ser Cys Arg Glu Arg Asn Gln Gly Ala
370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
            405                 410                 415

Cys Leu Asn Arg Gly Pro Ser Arg Met Cys Arg Cys Arg Pro Gly Phe
        420                 425                 430

Thr Gly Thr Tyr Cys Glu Leu His Val Ser Asp Cys Ala Arg Asn Pro
    435                 440                 445

Cys Ala His Gly Gly Thr Cys His Asp Leu Glu Asn Gly Leu Met Cys
450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
            485                 490                 495

Thr Asp Leu Ser Thr Asp Thr Phe Val Cys Asn Cys Pro Tyr Gly Phe
        500                 505                 510

Val Gly Ser Arg Cys Glu Phe Pro Val Gly Leu Pro Pro Ser Phe Pro
    515                 520                 525

Trp Val Ala Val Ser Leu Gly Val Gly Leu Ala Val Leu Leu Val Leu
530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
            565                 570                 575

Asp Asn Leu Ile Pro Ala Ala Gln Leu Lys Asn Thr Asn Gln Lys Lys
        580                 585                 590

Glu Leu Glu Val Asp Cys Gly Leu Asp Lys Ser Asn Cys Gly Lys Gln
    595                 600                 605

Gln Asn His Thr Leu Asp Tyr Asn Leu Ala Pro Gly Pro Leu Gly Arg
610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
            645                 650                 655
```

```
Ala Ile Cys Ser Pro Arg Asp Ser Met Tyr Gln Ser Val Cys Leu Ile
            660                 665                 670

Ser Glu Glu Arg Asn Glu Cys Val Ile Ala
            675                 680
```